(12) United States Patent
Uto et al.

(10) Patent No.: US 7,724,360 B2
(45) Date of Patent: May 25, 2010

(54) METHOD AND APPARATUS FOR INSPECTING FOREIGN PARTICLE DEFECTS

(75) Inventors: Sachio Uto, Yokohama (JP); Hiroyuki Nakano, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 12/273,174

(22) Filed: Nov. 18, 2008

(65) Prior Publication Data

US 2009/0079973 A1    Mar. 26, 2009

Related U.S. Application Data

(63) Continuation of application No. 11/325,548, filed on Jan. 5, 2006, now Pat. No. 7,453,561.

(30) Foreign Application Priority Data

Mar. 11, 2005    (JP) .............................. 2005-068340

(51) Int. Cl.
G01N 21/00    (2006.01)
(52) U.S. Cl. ............... 356/237.3; 356/237.1; 356/237.2
(58) Field of Classification Search .... 356/237.1–237.5
See application file for complete search history.

(56) References Cited

U.S. PATENT DOCUMENTS

| | | | |
|---|---|---|---|
| 4,806,774 A | 2/1989 | Lin et al. | |
| 5,220,617 A | 6/1993 | Bird et al. | |
| 2002/0154297 A1* | 10/2002 | Noguchi et al. | .......... 356/237.3 |
| 2004/0095573 A1 | 5/2004 | Tsai et al. | |
| 2005/0052643 A1 | 3/2005 | Lange et al. | |
| 2005/0110987 A1 | 5/2005 | Furman et al. | |

FOREIGN PATENT DOCUMENTS

| | | |
|---|---|---|
| JP | 62-089336 | 4/1987 |
| JP | 63-135848 | 6/1988 |
| JP | 01-117024 | 5/1989 |
| JP | 01-250847 | 10/1989 |
| JP | 2000-105203 | 4/2000 |
| JP | 2001-060607 | 4/2000 |

* cited by examiner

*Primary Examiner*—Michael P Stafira
(74) *Attorney, Agent, or Firm*—Antonelli, Terry, Stout & Kraus, LLP.

(57) ABSTRACT

The invention relates to a device production process for forming a circuit pattern on a substrate such as semiconductor device. To enable a stable inspection of a minute foreign particle and a pattern defect occurring in manufacture of a device at a high speed and with a high sensitivity, an object to be inspected on which a transparent film is formed, is irradiated with a beam which is emitted from an illuminator whose illumination direction and illumination angle are selected from a plurality of choices to be optimum, so that scattered reflected light from a minute foreign particle defect on the object or the transparent film is effectively detected by eliminating a noise from the pattern formed on the object, and a detection optical system is optimized by evaluating and adjusting, with an image forming performance checker, an image forming performance of the detection optical system included in an inspecting apparatus.

16 Claims, 14 Drawing Sheets

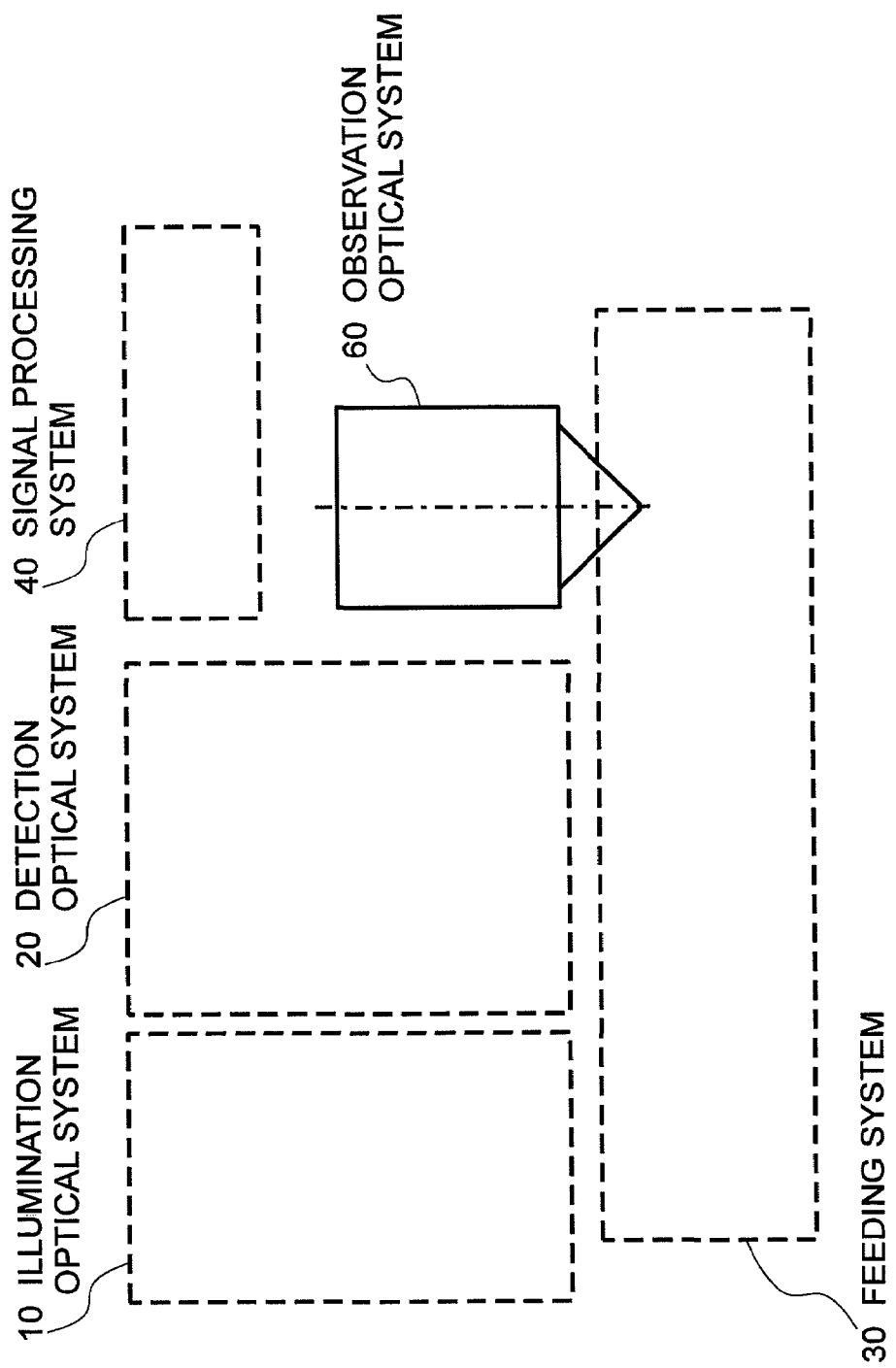

METHOD AND APPARATUS FOR INSPECTING FOREIGN PARTICLE DEFECTS

CROSS REFERENCE TO RELATED APPLICATION

This application is a Continuation of U.S. application Ser. No. 11/325,548, filed Jan. 5, 2006, now U.S. Pat. No. 7,453,561, which claims priority from Japanese Patent Application No. JP 2005-068340, filed Mar. 11, 2005, the contents of which are incorporated herein by reference.

BACKGROUND OF THE INVENTION

The present invention relates to a method and apparatus for inspecting, in a process of manufacturing a semiconductor device, foreign particles or a state of occurrence of defects, which method and apparatus is relevant to a step of detecting, analyzing, and taking measures against a foreign particle on a thin film substrate, semiconductor substrate, photomask, and other objects that are produced in manufacture of a semiconductor chip or a liquid crystal product, as well as a defect in a circuit pattern in the thin film substrate, semiconductor substrate, photomask and others.

In a process of producing a semiconductor device, a foreign particle present on a semiconductor substrate or a wafer leads to a defect such as defective insulation of wiring and short-circuit. With a recent trend of miniaturization of semiconductor devices, a minute foreign particle could be a cause of defective insulation of a capacitor or damage of a gate oxide film or others. Such a foreign particle is produced and introduced in various ways. For instance, the foreign particle may come from a movable portion in a feeding device or a human body, may be generated as a reaction product in a processing apparatus during a process using a process gas, or may come from chemicals or materials.

Similarly, in a process of producing a liquid crystal display element, when a defect is caused in a pattern by the foreign particle introduced in the above-described manner, the finished display element does not work. With a process of producing a printed circuit board or a printed wiring board, the circumstances is the same, namely, introduction of a foreign particle causes a short-circuit in a pattern or a bad connection. Hence, in manufacture of semiconductor devices, one (or more in some situations) foreign particle inspecting apparatus is disposed in each production line so as to detect a foreign particle at an early stage and feed back a result of the detection, in order to improve the yield rate.

One of techniques of this kind to detect a foreign particle on a semiconductor substrate is disclosed in JP-A-62-89336, which teaches to irradiate a semiconductor substrate with a laser beam and detect scattered light from a foreign particle adhering to the semiconductor substrate. The result of the inspection is compared with a result of an inspection last performed for the same kind of semiconductor substrate, so as to eliminate the possibility of misdetection of a pattern and enable a highly sensitive and reliable inspection of foreign particle defects. Disclosed in JP-A-63-135848, there is known another technique in which a semiconductor substrate is irradiated with a laser beam and scattered light from a foreign particle adhering to the semiconductor substrate is detected, and the detected foreign particle is analyzed by a method such as laser photoluminescence spectroscopy and secondary X-ray analysis (XMR).

As a technique to inspect foreign particles as mentioned above, there is known a method such that a wafer is irradiated with coherent light, and light emitted from a repetitive or periodic pattern on the wafer is removed by a spatial filter so that a foreign particle and a defect that are irregular or not periodic are emphasized to be detectable. Further, JP-A-1-117024 discloses a foreign particle inspecting apparatus where light is emitted toward a circuit pattern on a wafer in a direction 45-degree inclined with respect to directions of straight segments of principal groups in the circuit pattern and the zeroth-order diffraction light from the straight segments of the principal group is prevented from entering an aperture of an objective lens. The publication JP-A-1-117024 also teaches to block light emitted from straight segments of the other group than those of the principal groups by a spatial filter.

A technique related to an apparatus and method for inspecting a defect such as presence of a foreign particle is disclosed in JP-A-1-250847 and JP-A-2000-105203. The publication JP-A-2000-105203 teaches to change a pixel size at which detection is performed, by enabling switching associated with the detection optical system used for the detection, and to inspect a foreign particle by illuminating a substrate with light condensed in one direction. JP-A-2001-60607 discloses a technique to measure a size of a foreign particle.

However, any of the above-described conventional techniques does not succeed to detect with ease, at a high speed, and with a high sensitivity, a minute foreign particle or defect on a substrate on which a periodic pattern and a non-periodic pattern are present in a mixed manner. That is, the conventional techniques can not solve a problem that at a portion other than a periodic pattern such as memory cell portion, the detection sensitivity is low, or a minimum particle size detectable is large. Further, according to the conventional techniques, the detection sensitivity for a minute foreign particle or a defect on the order of 0.1 μm in an area where the pattern density is high is low. Still further, the detection sensitivity is low for a foreign particle or a defect that causes a short-circuit between wires, and for a foreign particle in the form of a thin film. The conventional technique disclosed in JP-A-2001-60607 has drawbacks that the measuring accuracy and precision for a foreign particle or a defect is low, and the detection sensitivity for a foreign particle on a wafer coated with a thin transparent film is low.

SUMMARY OF THE INVENTION

The invention has been developed in view of the above-described problems and thus an object of the invention is to provide a defect inspecting method and apparatus capable of inspecting a minute foreign particle or defect on the order of 0.1 μm on a substrate as an object of inspection in which a periodic pattern and a non-periodic pattern are present in a mixed manner, at a high speed and with a high accuracy and precision, and more particularly a method and apparatus for stably detecting a defect by using a plurality of defect inspecting apparatuses of the same structure in a production line of semiconductor devices or others, by reducing a variation in the performance among the detecting apparatuses.

Thus, the invention provides an apparatus for inspecting a foreign particle defect, comprising:
  an illuminator which irradiates a surface of a sample with an illuminating beam;
  a detector which collects through an objective lens scattered reflected light from the surface of the sample as illuminated by the illuminator and detects the collected light with a detecting device; and
  a signal processor which processes a signal obtained as a result of the detection of the scattered reflected light by the detecting device of the detector so as to detect a defect on the surface of the sample, wherein the detector includes a converging optical system which collects the scattered reflected light from the surface of the sample, and an aberration corrector which corrects an aberration of the converging optical system.

The illuminator has a first illuminating portion which irradiates the surface of the sample with an illuminating beam from a high angle, and a second illuminating portion which irradiates the surface of the sample with an illuminating beam from a low angle.

The converging optical system of the detector includes a reflection optical system and a refraction optical system, and the aberration corrector corrects the aberration of the converging optical system by changing a condition of reflection of the reflection optical system or a condition of refraction of the refraction optical system.

The converging optical system of the detector further includes an image forming magnification changer which changes an image forming magnification of the converging optical system while a position of the objective lens relatively to the detecting device is fixed.

The illuminating beam emitted from the illuminator toward the surface of the sample is formed in a shape long in a direction, and emitted from a direction oblique to the surface of the sample.

Further, the detector is adapted such that a relative distance between a substrate to be inspected and the detecting device is fixed and the image forming magnification is variable. An image forming optical system of the detector is adapted such that a size of a Fourier transform image is fixed while the image forming magnification is variable.

The invention also provides an apparatus for inspecting a foreign particle defect, comprising:
an illumination optical system including an illumination light source which emits an illuminating beam toward a surface of a substrate to be inspected, an angle of the illuminated beam being switchable between a high angle and a low angle;
a detection optical system including: an objective lens which is disposed at a position optimum for collecting scattered reflected light from a foreign particle defect on the substrate and collects the scattered reflected light from the foreign particle defect; an image forming optical system which forms an image of the scattered reflected light as collected by the objective lens; and a light detecting device which receives the image of the scattered reflected light formed by the image forming optical system, and converts the image into an image signal;
an A/D converting portion which converts the image signal obtained by the light detecting device of the detection optical system when the illumination optical system emits the illuminating beam at the high angle or the low angle, into a digital image signal;
a defect detecting and processing portion which detects a foreign particle defect based on the digital image signal; and
a confirming device which enables to confirm the detected foreign particle defect.

The defect inspecting apparatus according to the invention includes a measurer which measures an aberration of the detection optical system and a corrector which corrects the aberration, so as to enable a stable detection of defect, and a comparison is made between current data on the detection optical system and data thereon at the time of installation of the detection optical system in the defect inspecting apparatus, and a correction is made based on a result of the comparison, in order to enable a stable detection of a foreign particle defect for a long term, as well as reduce a performance variation among a plurality of the defect inspecting apparatuses having the same structure. Thus, it is enabled to reduce diffracted light from the circuit pattern on the substrate such as LSI pattern, thereby enabling an inspection of a minute foreign particle or a defect, a minute foreign particle or a defect that short-circuits the wires, and a thin film-like foreign particle, at high speed and with high accuracy and precision.

These and other objects, features and advantages of the invention will be apparent from the following more particular description of preferred embodiments of the invention, as illustrated in the accompanying drawings.

BRIEF DESCRIPTION OF THE DRAWINGS

FIG. 17 is a schematic diagram of the defect inspecting apparatus including an observation optical system.

DESCRIPTION OF THE PREFERRED EMBODIMENTS

Hereinafter, there will be described one embodiment of the invention, by referring to the accompanying drawings.

A defect inspecting apparatus according to the invention detects with a high sensitivity and at a high speed foreign particles and various kinds of defects such as pattern defect and microscratch on various kinds of substrates such as wafer as an object of a defect detection in various steps in a production process. In particular, the defect inspecting apparatus stably detects defects on a thin film formed on a wafer by distinguishing the defects from defects inside the thin film.

Figure 2A:
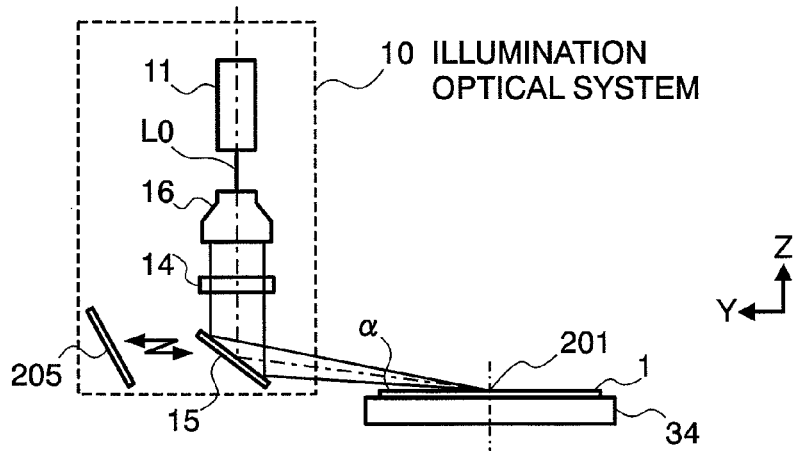
FIG. 2A is a schematic view of an illumination optical system of the defect inspecting apparatus shown in FIG. 1.

That is, the defect inspecting apparatus of the invention is adapted such that an illumination angle α and an illumination direction φ of a slit-like beam 201 emitted from an illumination optical system 10, as shown in FIG. 2A, are changeable depending on an object to be inspected, a detection optical system 20 is disposed such that a relative positional relationship between a surface of the object to be inspected and a light receiving surface of a light detecting device 26 is set such that an image of the surface of the object is formed on the light receiving surface, and an image forming magnification of the detection optical system 20 is variable so that an inspection can be made at a detection pixel size suitably set depending on a size of a defect to be detected.

Further, the defect inspecting apparatus has a function to distinguish different kinds of detected defects by using, as a characteristic quantity, a difference in scattered light from defects illuminated with an illumination beam from a plurality of illumination angles, for instance.

Initially, a defect inspecting apparatus according to one embodiment of the invention will be described in detail. In the embodiment below, the invention is applied to an inspection of a minute or large foreign particle and a microscratch on a semiconductor wafer or a transparent film formed thereon, a foreign particle in the transparent film, and a defect such as pattern defect. However, the object to be inspected by an apparatus or a method according to the invention is not limited to a semiconductor wafer but may be a thin film substrate, photomask, TFT, or PDP, for instance.

Figure 1:
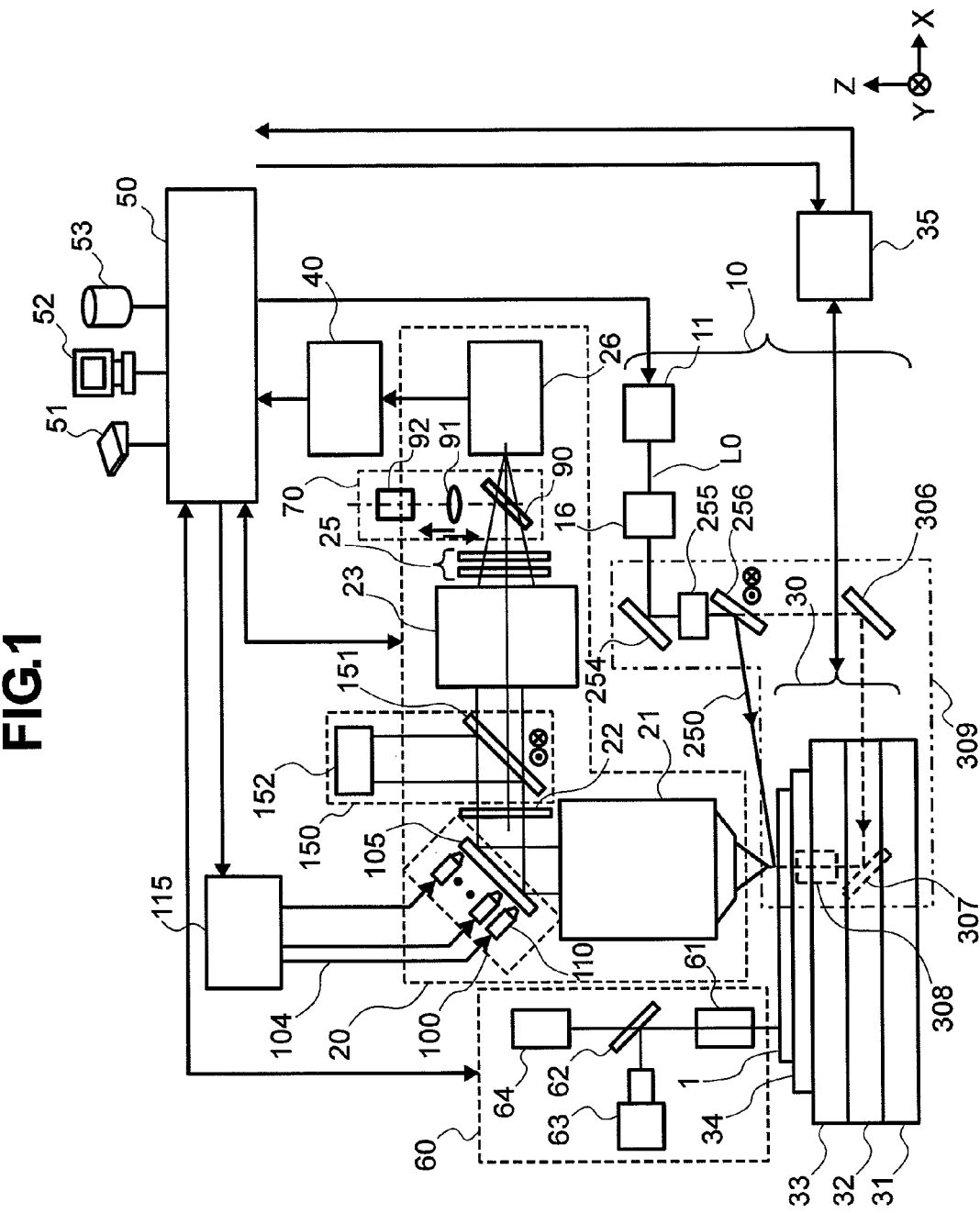
FIG. 1 is a schematic diagram of a defect inspecting apparatus according to one embodiment of the invention.

FIG. 1 shows a structure of a defect inspecting apparatus according to the embodiment of the invention. This defect inspecting apparatus includes an illumination optical system 10, a magnification-variable detection optical system 20, a feeding system 30, a signal processing system 40 and a general controller 50 for an overall control of the defect inspecting apparatus.

The feeding system 30 includes an XY-stage 31, a Z-stage 32, and a φ-stage 33, for placing on a sample table 34 a wafer 1 as an example of a substrate to be inspected, and displacing the wafer 1. The feeding system 30 further includes a controller 35 for controlling theses stages 31, 32, 33. The wafer 1 may be of various kinds seen in various production steps.

The illumination optical system 10 includes a laser light source 11, a beam expander optical system 16, mirrors 254, 256, and a lens 255, and enlarges light as emitted from the laser light source 11 to a size by the beam expander optical system 16, and irradiate the wafer 1 with the enlarged beam in a plurality of oblique directions via the mirrors 254, 256, the lens 255, and others.

The detection optical system 20 includes an objective lens 21, a reflection varying unit 100, a spatial filter 22, an image forming lens 23, an optical filter 25, a light detecting device 26 such as TDI image sensor.

In an optical path of the detection optical system 20, a wavefront measuring optical system 150 is disposed. The wavefront measuring optical system 150 includes a mirror 151 and a detecting device 152. The mirror 151 is movable between a position in the optical path of the detection optical system 20 and another position retracted from the optical path. A parallel light flux emitted from the wafer 1 is incident on the objective lens 21 and detected by the detecting device 152 by way of the mirror 151, when an image forming performance of the optical system 20 is checked.

A signal processing system 40 processes an image signal detected by the light detecting device 26 so as to detect a defect and a foreign particle.

An observation optical system 60 includes a lens 61, a polarizing beam splitter 62, an illumination light source 63, and an imaging device 64, and illuminates a surface of the wafer 1 by the illumination light source 63, so as to confirm the presence/non-presence and the shape of a foreign material as detected in advance by another inspecting apparatus.

The general controller 50 operates to set conditions of an inspection and generally controls the illumination optical system 10, the magnification-variable detection optical system 20, the feeding system 30, and the signal processing system 40. The general controller 50 includes an input/output device 51 including a keyboard and a network, a display device 52, and a memory device 53.

The defect inspecting apparatus further includes an autofocus control system (not shown) which makes an image on the wafer 1 to be formed on a light receiving surface of the light detecting device 26.

This defect inspecting apparatus is adapted such that the wafer 1 can be irradiated with an illumination beam from a plurality of directions. As shown in FIG. 2A, the illumination optical system 10 includes the beam expander optical system 16, a lens 14, and a mirror 15. The beam expander optical system 16 may include a concave lens and a convex lens, for instance, and enlarges a beam L0 as emitted from the laser light source 11.

Figure 2B:
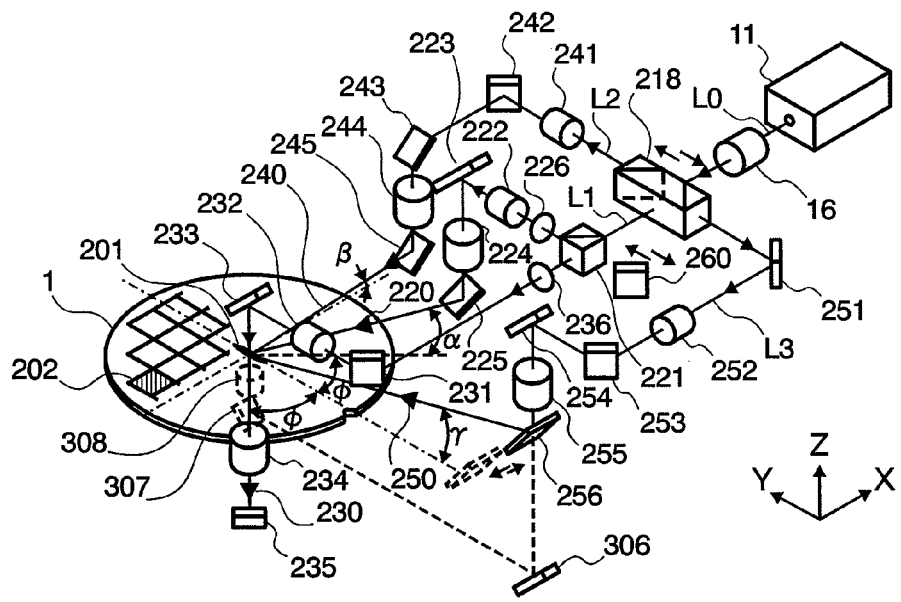
FIG. 2B is a perspective view illustrating how the illumination optical system is constructed.
Figure 2C:
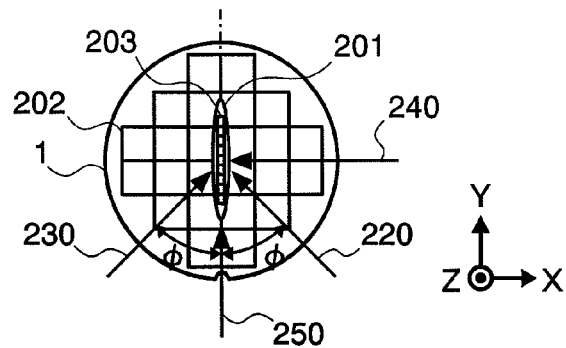
FIG. 2C is a plan view of a wafer as illuminated by the illumination optical system.

As shown in FIGS. 2B and 2C, the defect inspecting apparatus is capable of emitting a slit-like beam 201 toward the wafer 1 as an object to be inspected and put on a sample table 34, in a plurality of directions in plan view, namely, four directions 220, 230, 240 and 250 as shown in FIGS. 2B and 2C, and at a plurality of illumination angles.

The reason why the illumination beam 201 is slit-like is that light scattered from a foreign particle or a defect when the wafer 1 is illuminated is detected at once by a row of light receiving elements in the light detecting device 26, so that the speed of the foreign particle/defect inspection is enhanced.

An orientation of the wafer 1 on the table 34 is adjusted such that the O-stage 33 is moved so that directions of a row and a column of a matrix of chips 202 on the wafer 1 coincide with directions of movement of the XY-stage 31. The slit-like beam 201 is emitted toward the wafer 1 whose orientation has been thus adjusted.

Figure 3A:
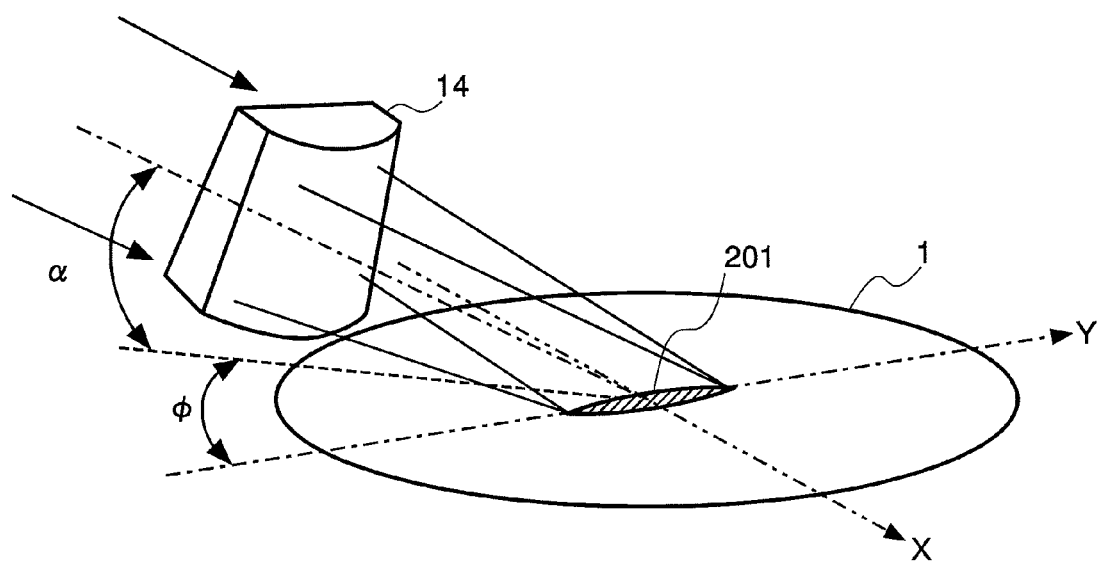
FIG. 3A shows a state where the wafer is irradiated with a laser beam from a direction at an angle $\phi$ with respect to a scanning direction of a Y-stage, i.e., a Y-axis direction of the wafer, and at an angle $\alpha$ with respect to a Z-axis direction of the wafer, to form a slit-like beam on the wafer.

The slit-like beam 201 emitted toward the wafer 1 is adjusted by an optical system which converges light in an X-axis direction (which is one of two directions in which the XY-stage 31 is movable) and directs the light into parallel rays in a Y-axis direction (which is the other direction in which the XY-state 31 is movable), such that an optical axis of the beam 201 is perpendicular to the X-axis direction, and parallel to the Y-axis as well as a direction of alignment 203 (shown in FIG. 2C) of pixels of the light detecting device 26. Thus, a longitudinal direction of the slit-like beam 201 incident on the wafer 1 is perpendicular to the X-axis direction, and parallel to the Y-axis direction. This arrangement facilitates alignment among the chips when a comparison is made among image signals representative of the chips. Such a slit-like beam 201 can be formed by disposing a conical lens 14 or a cylindrical lens 244, for instance, in the optical path, as shown in FIGS. 3A and 3B.

To form the slit-like beam 201 on the wafer 1 when the illumination is made from a direction 220 or 230, a laser beam is emitted from a direction at an angle $\phi$ with respect to the Y-axis direction on one of two opposite sides (i.e., on the left or right side in FIG. 2C), and inclined at angle $\alpha$ in the Z-axis direction. In FIG. 2B, a first segment of the optical path of the illumination beam from the direction 230, which is from a mirror 233 to a mirror 235 via a cylindrical lens 234, and a second segment thereof which is from the mirror 235 to an area irradiated with the slit-like beam 201 on the wafer 1, overlap. To realize such illumination, a lens 14 (shown in FIG. 3 and corresponding to cylindrical lenses 224, 234 in FIG. 2B) having a conical curved surface whose radius of curvature in a longitudinal direction continuously varies is disposed in the optical path, so that the longitudinal direction of the slit-like beam 201 is parallel to the Y-axis direction.

Figure 3B:
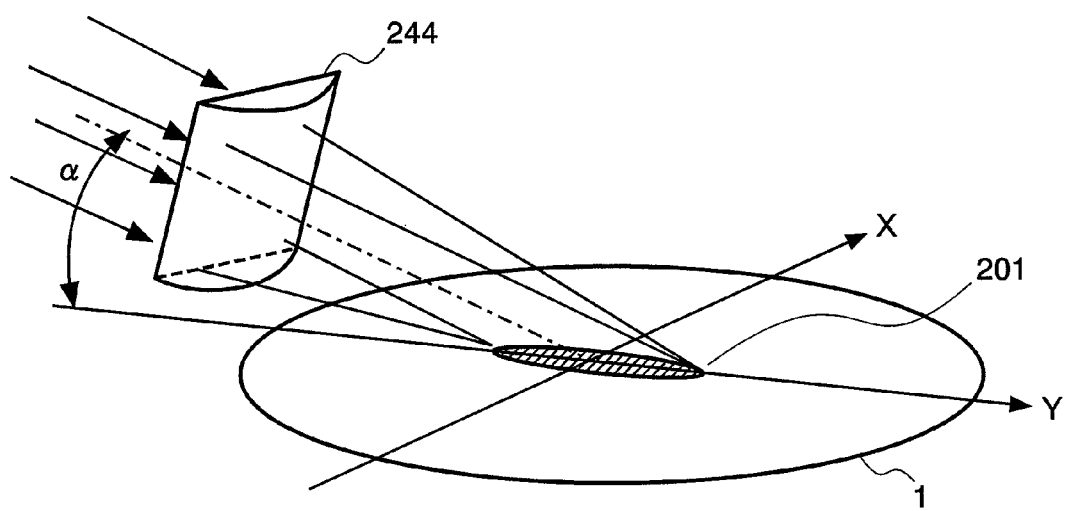
FIG. 3B shows a state where the wafer is irradiated with a laser beam from a direction that is parallel to the Y-axis direction to form the slit-like beam on the wafer, with a longitudinal direction of the slit-like beam parallel to the direction from which the laser beam is incident.

When the illumination is made from a direction 250, the wafer 1 is illuminated in a direction parallel to the Y-axis direction and the longitudinal direction of the slit-like beam 201, and the beam 201 can be formed in the slit-like shape by being passed through a cylindrical lens 255 (having the same shape as the cylindrical lens 244 shown in FIG. 3B).

When the illumination is made from a direction 240, the wafer 1 is illuminated in a direction parallel to the Y-axis direction and perpendicular to the longitudinal direction of the slit-like beam 201, and thus the beam 201 can be formed in the slit-like shape by being passed through a cylindrical lens 244 disposed at an angle of 90 degrees with respect to the cylindrical lens 255.

The illumination optical system 10 is constructed such that the mirror 15 and a mirror 205 are switchable based on an instruction from the general controller 50, as shown in FIG. 2A, so that the illumination angle $\alpha$ is changeable depending on the kind of foreign particle on the wafer 1 to be inspected, for instance. As shown in FIG. 2C, the slit-like beam 201 has an illuminating area covering the row 203 of the pixels of the light detecting device 26, regardless of what the illumination angle is. That is, the position the slit-like beam 201 is incident on the wafer 1 is constant irrespective of from which direction the illumination beam is incident, even where the direction of the incidence is not one of the above-mentioned directions, such as when the incident direction is a direction opposite to the direction 220 or 230.

Thus, an illumination with parallel light in the Y-axis direction and at an angle $\phi$ of about 45 degrees is achieved. By having the slit-like beam 201 in the form of the parallel light in the Y-axis direction, diffracted light from a circuit pattern whose straight segments of a main group is oriented in the X-axis or Y-axis direction is blocked by the spatial filter 22.

The conical lens 14 may be produced according to a production method disclosed in JP-A-2000-105203, for instance.

The present defect inspecting apparatus is constructed such that the slit-like beam 201 is formable on the wafer 1 from a plurality of illumination angles, in order to enable detection of various kinds of foreign particles and defects on the wafer 1. That is, an object of inspection by the apparatus is a defect of a pattern on the wafer 1 and a foreign particle whose height is small.

With an increase in the illumination angle $\alpha$, an amount of the reflected diffracted light from the circuit pattern increases and the S/N ratio decreases, and thus an empirically obtained optimum angle is employed. For example, when a foreign particle having a small height is to be detected, the illumination angle $\alpha$ is preferably small, e.g., about 1 to 10 degrees, and more preferably about 1 to 5 degrees. In another case where a foreign particle between wires or a pattern defect is to be detected in a wiring step, the illumination angle $\alpha$ is preferably large, i.e., about 40 to 60 degrees, and more preferably 45 to 55 degrees, taking account of the S/N ratio related to the difference between the pattern and the foreign particle/defect. Where there is a fixed correspondence between a step in which the inspection is implemented and the kind of foreign particle/defect desired to be detected, the illumination angle may be predefined in an inspection recipe. To detect a foreign particle/pattern defect on the wafer evenly, the illumination angle may be set at a value between the above-mentioned values, that is, a value between 5 and 45 degrees.

When the inspection is performed in a wiring step, the illumination direction $\phi$ is preferably aligned with the wiring pattern formed on the wafer so as to facilitate detection of a foreign particle between wires. Where the circuit pattern on the wafer is not a wiring pattern but is constituted by contact holes, capacitors, and/or others, there is no specific orientation in the circuit pattern, and thus it is desirable that the illumination beam is incident in a direction of about 45 degrees with respect to a chip in question. A change in the illumination angle is made, for instance, by switching between two mirrors 15, 205 inclined at different angles, as shown in FIG. 2, or by rotating the mirror 15 (or 205) around an axis extending in the X-axis direction perpendicular to a surface of the sheet in which the FIG. 2A is presented, by means of a rotating device (not shown). The mirror 15 is moved in the Z-axis direction also so that the slit-like beam 201 is aligned on the wafer 1 with a detection optical axis of the detection optical system, and the lens 14 is also adjusted or moved in the Z-axis direction so that the slit-like beam 201 has a minimum diameter on the detection optical axis of the detection optical system.

There will be now described how to change the illumination direction, by referring to FIG. 2B. In FIG. 2B, reference numeral 218 denotes a splitting optical element consisting of a mirror, a prism, and others. The splitting optical element 218 is moved in the Y-axis direction by a drive means not shown, so as to allow the laser beam L0 as emitted from the laser light source 11 to pass through the element 218, or reflect the laser beam L0, to direct the beam in one of three directions. The laser beam L1 transmitted through the splitting optical element 218 is split into a transmitted component and a reflected component by a half prism 221. The transmitted component is, for instance, then transmitted through a wave plate 236 and reflected by a mirror 231, a beam diameter correction optical system 232, the mirror 233, the conical lens 234, and the mirror 235, so as to form the slit-like beam 201 on the wafer 1 from the direction 230.

On the other hand, the reflected light from the half prism 221 also forms the slit-like beam 201 on the wafer 1, via optical elements having the same functions as mentioned above with respect to the transmitted component from the half prism 221, namely, a beam diameter correction optical system 222, a wave plate 226, a mirror 223, a cylindrical lens 224, and a mirror 225. The beam diameter correction optical systems 222 and 232 adjust the beam diameter of the laser beam incident on the conical lens 14 so that the slit-like beam 201 incident on the wafer 1 has a constant size. When a mirror 260 is disposed in place of the half prism 221, illumination is possible only from the direction 220, while when neither the half prism 221 nor the mirror 260 is used, illumination is possible only from the direction 230. By disposing wave plates 226, 236 in both the optical paths on the rear side of the half prism 221, the polarizing direction of the emitted laser beam can be made the same.

A laser beam L2 reflected by the splitting optical element 218 is transmitted through the beam diameter correction optical system 241, then reflected by mirrors 242 and 243, transmitted through a cylindrical lens 244, and again reflected by a mirror 245, so as to form the slit-like beam 201 on the wafer 1 from the direction 240.

A laser beam L3 also forms the slit-like beam 201 on the wafer 1 from the direction 250, via optical elements similar to those in the optical path of the laser beam L2, namely, a mirror 251 which reflects the beam L3, a beam diameter correction optical system 252 which transmits the laser beam L3, mirrors 253 and 254 that reflect the laser beam L3, the cylindrical lens 255, and a mirror 256 which reflects the laser beam L3.

For instance in a wiring step and where a wiring pattern formed on the wafer includes many segments extending in the X-axis direction or the Y-axis direction, the direction 240 or 250 of illumination coincides with the direction in which many segments of the wiring pattern extend, thereby facilitating detection of a foreign particle between wires.

In the present embodiment, a high-power YAG laser of 532 nm second harmonic wavelength is used as the laser light source 11. However, it is not essential that the wavelength be 532 nm, but an UV laser, a deep UV laser, or a vacuum UV laser may be employed. Further, the light source may be other lasers such as Ar laser, nitrogen laser, He—Cd laser, excimer laser, and semiconductor laser.

In general, a decrease in the wavelength of the laser improves a resolution of a detected image, thereby enabling a highly sensitive inspection.

Figure 4A:
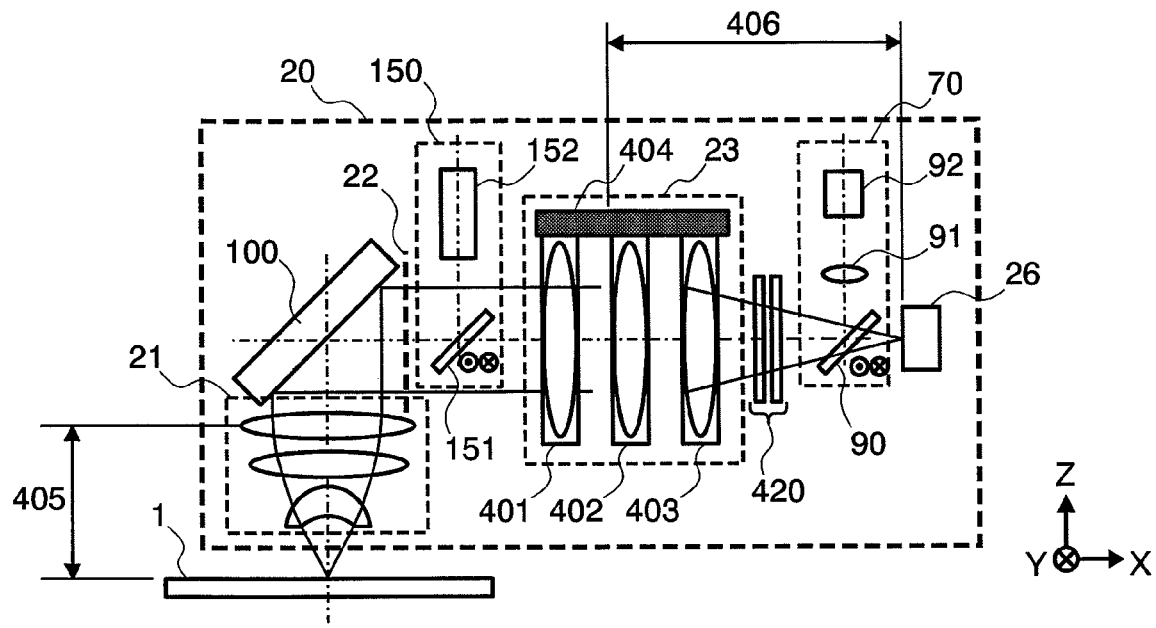
FIG. 4A is a schematic view of a detection optical system of the defect inspecting apparatus.

There will be next described the detection optical system 20 shown in FIG. 4A. The detection optical system 20 is constructed such that reflected diffracted light from the object substrate in the form of the wafer 1 is detected by the light detecting device 26 such as TDI image sensor, via the objective lens 21, the reflection varying unit 100, the spatial filter 22, the image forming lens (magnification-variable image forming optical system) 23, a density filter, an optical filter group 420 including a polarizing plate. When a TDI sensor is used as the light detecting device 26, the TDI sensor may be one having a plurality of output taps to output a plurality of signals in parallel, so that the signal processing system 40 processes the signals in parallel using a plurality of processing circuits and a plurality of processing programs, thereby enabling a detection at high speed.

The spatial filter 22 operates to block a Fourier transform image of the reflected diffracted light from a periodic pattern on the wafer 1 and allows scattered light from a defect/foreign particle to pass therethrough. The spatial filter 22 is disposed at an image forming position (corresponding to an exit pupil) with respect to the objective lens 21 in the spatial frequency domain, i.e., the Fourier transformation.

Figure 5A:
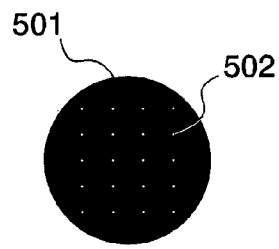
FIG. 5A is a view of an image of reflected diffracted light from a periodic pattern on the wafer in a field of vision of a pupil observation optical system of the defect inspecting apparatus.
Figure 5B:
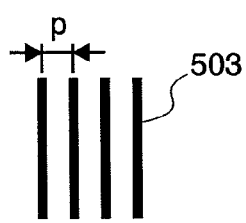
FIG. 5B shows a light blocking pattern of a spatial filter.
Figure 5C:
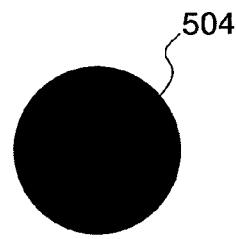
FIG. 5C is a view of the field of vision when the image of the reflected diffracted light is filtered with the spatial filter.

Adjusted as follows, the spatial filter 22 is disposed in the optical path of the detection optical system 20. Initially, using a pupil observation optical system 70 including a mirror 90 that is retracted in the X-axis direction during an inspection, a projector lens 91, and a TV camera 92, an image 502 of the reflected diffracted light from a periodic pattern, at the image forming position of the Fourier transformation in a field of view 501 of the pupil observation optical system 70, is taken, as indicated by white points in FIG. 5A, for instance. Then, intervals p of rectangular light blocking portions of a screen 503 as shown in FIG. 5B which is disposed at the image forming position of Fourier transformation is mechanically changed by a suitable mechanism (not shown) so that the rectangular light blocking portions block the image 502 of the reflected diffracted light. Thus, an adjustment is made to obtain an image 504 without a luminescent spot of the image of the reflected diffracted light from the pattern, as shown in FIG. 5C, at the image forming position of the Fourier transformation. These steps are implemented by the signal processing system 40 processing signals from the TV camera 92 based on an instruction from the general controller 50. The screen 503 is not limited to the above-described one, but may be replaced with a screen where the light blocking portions are formed on a transparent substrate using a liquid crystal display element, based on an image signal from the TV camera 92. That is, black portions as light blocking portions and white portions are made by operating the liquid crystal display element to form the light blocking portions suitable for the image taken by the TV camera 92.

The defect inspecting apparatus is operable in one of a high-speed mode to implement the inspection at a high speed, and a low-speed mode to implement the inspection at a low speed but with a high sensitivity. That is, where the circuit pattern on the object at an area to be inspected is formed in a high density, the magnification of the detection optical system is increased to obtain an image signal of high resolution, thereby enabling an inspection at high sensitivity. On the other hand, where the circuit pattern on the object at an area to be inspected is formed in a low density, the magnification of the detection optical system is decreased to enable an inspection at high speed while maintaining the high sensitivity. Thus, the size of foreign particle/defect to be detected and the detection pixel size are optimized, and only scattered light from the foreign particle/defect is efficiently detected with noise from materials other than foreign particle/defect eliminated. In this way, in the defect inspecting apparatus, the magnification of the detection optical system 20 disposed above the wafer 1 is made variable with a simple structure.

Figure 4B:
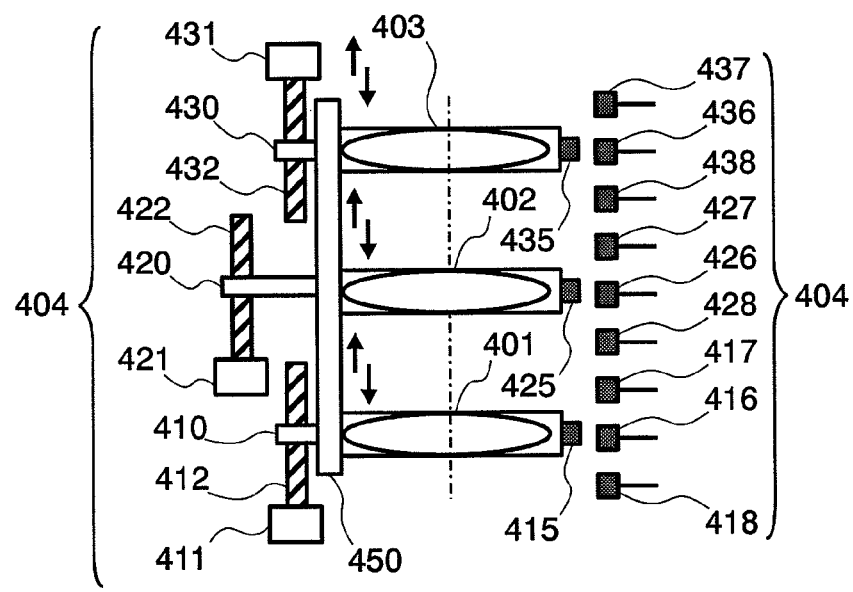
FIG. 4B is a schematic view of a magnification-variable image forming optical system of the detection optical system.

There will be described how to change the magnification of the detection optical system, by referring to FIGS. 4A and 4B.

A change in the magnification of the detection optical system is made based on an instruction from the general controller 50. The image forming lens 23 is constituted by movable lenses 401, 402, 403 and a moving mechanism 404. When the magnification is changed, the magnification of the image of the surface of the wafer as formed on the detecting device 26 is changeable without changing the positions of the objective lens 21 and the spatial filter 22 in a direction of the optical axis. That is, when the magnification is changed, a relative position between the object substrate (wafer) 1 and the light detecting device 26 needs not be changed. Thus, the moving mechanism 404 operated to change the magnification is simple in structure, and an area size of Fourier transformation is not changed, thereby making it unnecessary to replace the spatial filter 22.

The magnification M of the detection optical system 20 is obtained by the following equation 1, where $f_1$ represents a focal length 405 of the objective lens 21, and $f_2$ represents a focal length 406 of the image forming lens 23:

$$M = f_2/f_1 \quad (1)$$

Hence, to set the magnification of the magnification-variable detection optical system 20 at M, the movable lenses 401-403 are moved to positions that makes $f_2$ equal to $(M \times f_1)$, since $f_1$ is a constant.

There will be described in detail the moving mechanism 404 shown in FIG. 4A, by referring to FIG. 4B. FIG. 4B shows a detailed structure of the image forming lens 23 (shown in FIG. 4A) including the movable lenses 401-403 and the moving mechanism 404, and illustrates how to move and position the movable lenses 401, 402, 403 at specific positions. The movable lens 401 is held by a lens holder 410 that is movable on a linear guide 450 in a direction of the optical axis by driving a ball screw 412 by a motor 411. The movable lenses 402 and 403 are held by lens holders 420 and 430, respectively, and individually movable on the linear guide 450 by driving of ball screws 422, 432 by motors 421, 431.

Movable portions 415, 425, 435 of positioning sensors are disposed at ends of the respective lens holders 410, 420, 430 holding the movable lenses 401, 402, 403, while detecting portions 416-418, 426-428, 436-438 of the positioning sensors are disposed at positions where the movable lenses 401, 402, 403 are to be stopped. The stop positions correspond to respective magnification levels. The motors 411, 421, 431 are driven to move the lens holders in the direction of the optical axis and the lens holders are positioned by detecting the movable portions 415, 425, 435 of the positioning sensors by the detecting portions 416, 426, 436 that are at positions corresponding to a desired magnification. The positioning sensors 417, 418 are an upper limit sensor and a lower limit sensor for the movable lens 401 in the direction of the optical path, and each of the movable lenses 402, 403 also has the same limit sensors 427, 428 and 437, 438. The positioning sensors may be optical or magnetic sensors, for instance.

The moving mechanism 404 is operated based on an instruction from the general controller 50. That is, the magnification is set depending on information on a surface the object substrate 1 on the stage and the production process, so that minute foreign particles/defects are detectable as many as possible. For instance, where the circuit pattern on the object substrate 1 is formed in a high density, a mode for inspection at high magnification and with high sensitivity is selected, while where the circuit pattern is formed in a low density, a mode for inspection at low magnification and high speed is selected.

In this way, the detection optical system of the defect inspecting apparatus can cover a wide range of magnification with a single lens system. However, the number of lenses of a lens group constituting the detection optical system is increasing, and also there is an increasing demand for high surface precision and high assembly precision. In addition, there emerges a need to deal with mechanical vibrations in the defect inspecting apparatus and an environmental change such as temperature change.

Hence, the detection optical system of the defect apparatus according to the invention allows the illumination beam having the same wavelength as an inspection illumination beam, to pass the detection optical system, and detects a wavefront aberration of the transmitted light, thereby enabling to monitor the image formation performance of the optical system 20.

For instance, in the optical system shown in FIG. 2B, the laser beam L0 emitted from the laser light source 11 and passes through the beam expander optical system 16 is reflected by the splitting optical element 218. The reflected laser beam now denoted by L3 is reflected by the mirror 254, and incident on a condenser lens 308 via mirrors 306, 307, with the lens 255 and mirror 256 retracted from the optical path, so as to form, by the condenser lend 308 and on a back side of the wafer 1, a spot of light at the same position in the Z-axis direction as a place to be inspected on an upper side of the wafer 1.

A structure of an optical system 309 for monitoring the image formation performance of the detection optical system 20 is shown in FIG. 1 also. As shown in FIG. 2, the laser beam L0 travels from the mirror 306 toward the mirror 307 in the Y-axis direction. In FIG. 1, however, in the monitoring optical system 309, the laser beam is represented as if the beam travels from the mirror 306 to the mirror 307 along the X-axis direction, for the sake of convenience.

The laser spot formed by the condenser lens 308 passes through the objective lens 21 of the detection optical system 20 shown in FIG. 1, to become a parallel light flux, that is reflected by the reflection varying unit 100 and then by the mirror 151 disposed between the reflection varying unit 100 and the image forming lens 23 to be retractable from the optical path in the Y-axis direction, and is incident on the wavefront detecting device 152.

Figure 13A:
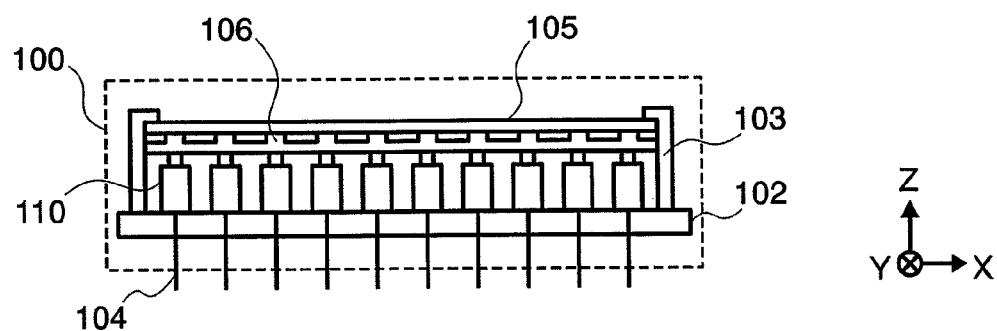
FIG. 13A is a schematic view of a reflection varying unit.

The reflection varying unit 100 includes a plurality of actuators 110 arranged in the X-axis and Y-axis directions on a support plate 102 as shown in FIG. 13A, a spacer 106, and a reflecting mirror 105. The actuators 110, spacer 106, and reflecting mirror 105 are fixed to the support plate 102 by a holder plate 103. Each actuator is, for instance, a piezoelectric element or a device directly driven by motor. A controller 115 converts electrical signals from a fringe analyzing apparatus 350 (shown in FIG. 6) into drive signals to drive the actuators 110.

Figure 13B:
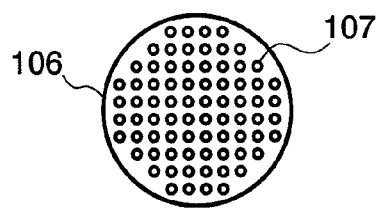
FIG. 13B shows one example of a spacer of the reflection varying unit on which spacer a plurality of protrusions are arranged.
Figure 13C:
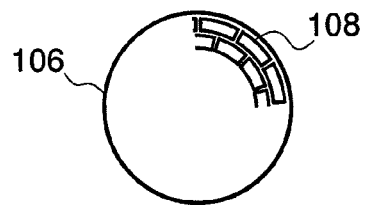
FIG. 13C shows another example of the spacer on which a plurality of sectorial, concentric protrusions are arranged.

The spacer 106 between the reflecting mirror 105 and the actuators 110 is an elastically deformable member, which has, for instance, a plurality of protrusions 107 as shown in FIG. 13B, or a plurality of protrusions arranged concentrically and along a circumference as shown in FIG. 13C. The actuators 110 are arranged so that a pressure acts on each of the protrusions. A reflecting surface of the reflecting mirror 105 is slightly deformed by a small displacing force or pressure corresponding to an electrical signal from the controller 115. The way of deforming the reflecting mirror is not limited to the above-described one, but there may be employed a mirror including a plurality of reflecting mirrors produced by a process of producing semiconductor devices or otherwise, and with an integrally formed driving system.

For instance, the wavefront detecting device 152 is a CCD camera where light receiving elements are arranged in a matrix, and the parallel light flux is focused on the light receiving elements by condenser lenses arranged in a matrix near a light receiving surface. For instance, where a wavefront of the parallel light flux is irregular because of an aberration of the optical system, output signals from the light receiving elements vary and a discontinuity occurs. The general controller 50 processes the image signal outputted from the wavefront detecting device 152 to calculate an amount of the wavefront aberration. A comparison is made between the calculated wavefront aberration and data on the lenses of the detection optical system 20 at the time of the production which data is stored in a storage device 53. When it is determined based on a result of the comparison that an aberration is present, the reflecting surface of the reflecting mirror 105 in the reflection varying unit 100 is adjusted by being deformed by operating the actuators 110 disposed on the back side of the reflecting surface. Then, the amount of the wavefront aberration is measured again. This process of adjusting the reflecting surface of the mirror 105 and measuring the aberration is repeated until an amount of the aberration lowers down below a predetermined threshold. The reflecting mirror 105 is disposed at a position of an exit pupil of the objective lens 21, for instance.

Figure 6:
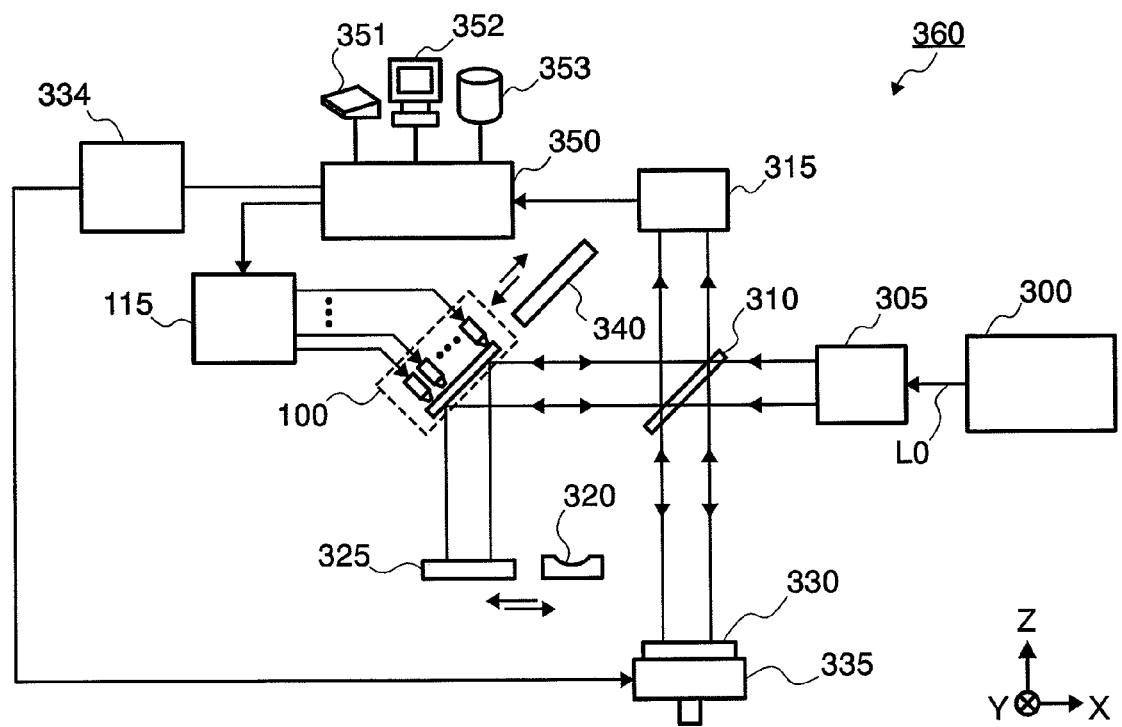
FIG. 6 is a block diagram of an interferometer apparatus according to the embodiment.

There will be now described an example of a method of adjusting the lenses of the detection optical system 20, by referring to FIGS. 6 to 13. FIG. 6 is a schematic diagram of an interferometer apparatus 360 that can adjust a lens aberration of the detection optical system 20 by measuring interference fringes for each of the objective lens 21 and the image forming lens 23.

That is, in the interferometer apparatus 360 shown in FIG. 6, a laser beam L0 emitted from a laser light source 300 is first enlarged to a size by a beam expander optical system 305, and then split by a half mirror 310 into a transmitted component and a reflected component. The component transmitted through the half mirror 310 is reflected by the reflection varying unit 100 (or the mirror 340) to be incident on a plane mirror 325 (or a spherical mirror 320). On the other hand, the component of the light reflected by the half mirror 310 enters a reference mirror 330. The reflection varying unit 100 and the mirror 340 are retractable from an optical path, and the plane mirror 325 and the spherical mirror 320 are retractable from an optical path, by respective mechanisms not shown. The two light beams respectively reflected by the plane mirror 325 and the reference mirror 330 return to the half mirror 310 along respective incoming optical paths. The light beam reflected by the plane mirror 325 is reflected by the half mirror 310, while the light beam reflected by the reference mirror 330 is transmitted through the half mirror 310, so that the two light beams overlap and enter the detecting device 315. The reference mirror 330 is placed on a fine adjustment stage 335 that is displaced in the Z-axis direction by a small amount based on a signal sent from the fringe analyzing apparatus 350 via a controller 334. Reference numerals 351, 352 and 353 respectively denote an input/output device, a display device, and a storage device.

Figure 9:
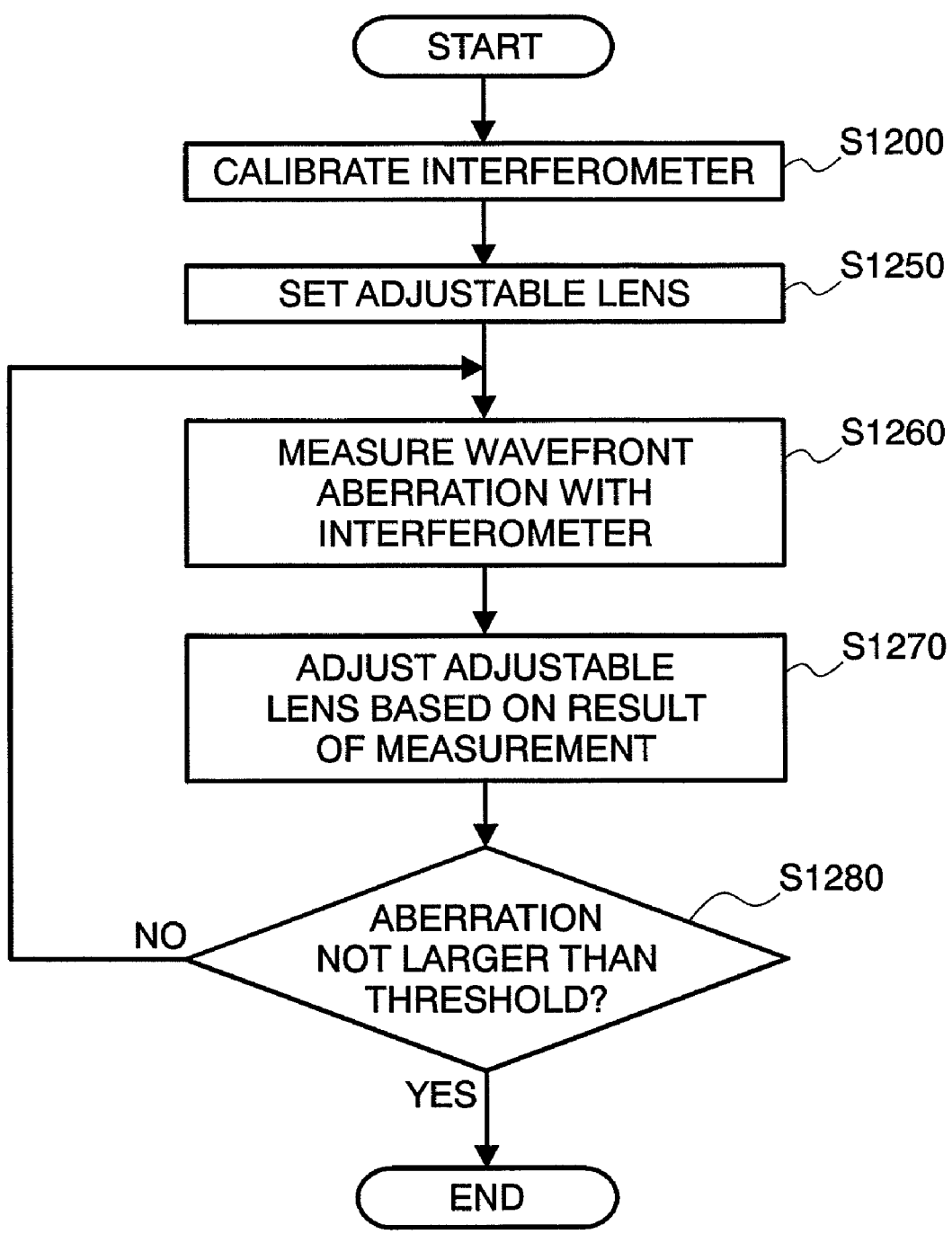
FIG. 9 is a flowchart illustrating a procedure of the adjustment of the rear lens group illustrated in FIG. 7.

Referring to a flowchart of FIG. 9, there will be described an example of a procedure of adjusting a rear lens group system 19 including the image forming lens 23 of the detection optical system 20, by using the interferometer apparatus 360.

Initially, as shown in FIG. 6, the reflection varying unit 100 is switched or replaced with the mirror 340 so that the mirror 340 is set in the optical path, and the plane mirror 325 is switched or replaced with the spherical mirror 320 so that the spherical mirror 320 is set in the optical path.

Then, with the beam expander optical system 305 retracted from the optical path, a laser beam emitted from the laser light source 300 is split by the half mirror 310 into two components that enter and reflected by the spherical mirror 320 and the reference mirror 330, respectively, and return along the incoming paths, to be reflected by or transmitted through the half mirror 310 and then synthesized. The synthesized beam is incident on detecting device 315. That the two components of the laser beam meet on the detecting device 315 is confirmed (S1200).

Figure 7:
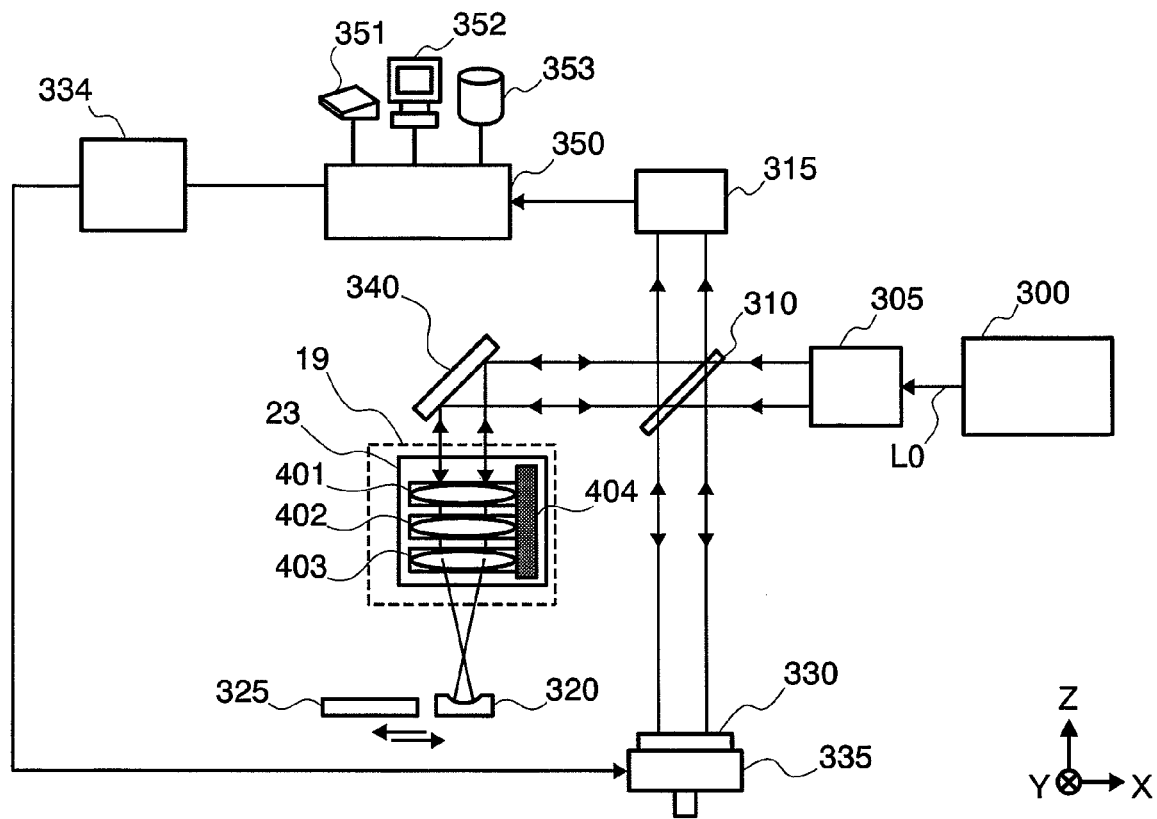
FIG. 7 illustrates how a rear lens group of the detection optical system is adjusted using the interferometer apparatus.

Then, as shown in FIG. 7, the beam expander optical system 305 is set in the optical path, and the rear lens group system 19 as an adjustable lens constructed such that the movable lenses 401-403 are incorporated in a lens barrel, is set such that an image forming position is located on the side of the spherical mirror 320 (S1250). The interval between the movable lenses 401-403 is set at an initial value.

Then, with the fringe analyzing apparatus 350, the wavefront aberration is measured (S1260). The adjustable lens 19 is adjusted based on the measured aberration, so that the shape of the interference fringes changes from that of FIG. 8A to that of the FIG. 8B on a monitor screen of the display device 352 (S1270). The aberration is again measured with the fringe analyzing apparatus 350, and it is determined whether the amount of the aberration is not larger than the predetermined threshold (S1280). When the amount of the aberration is larger than the threshold, the steps S1260-S1280 are repeated.

Figure 11:
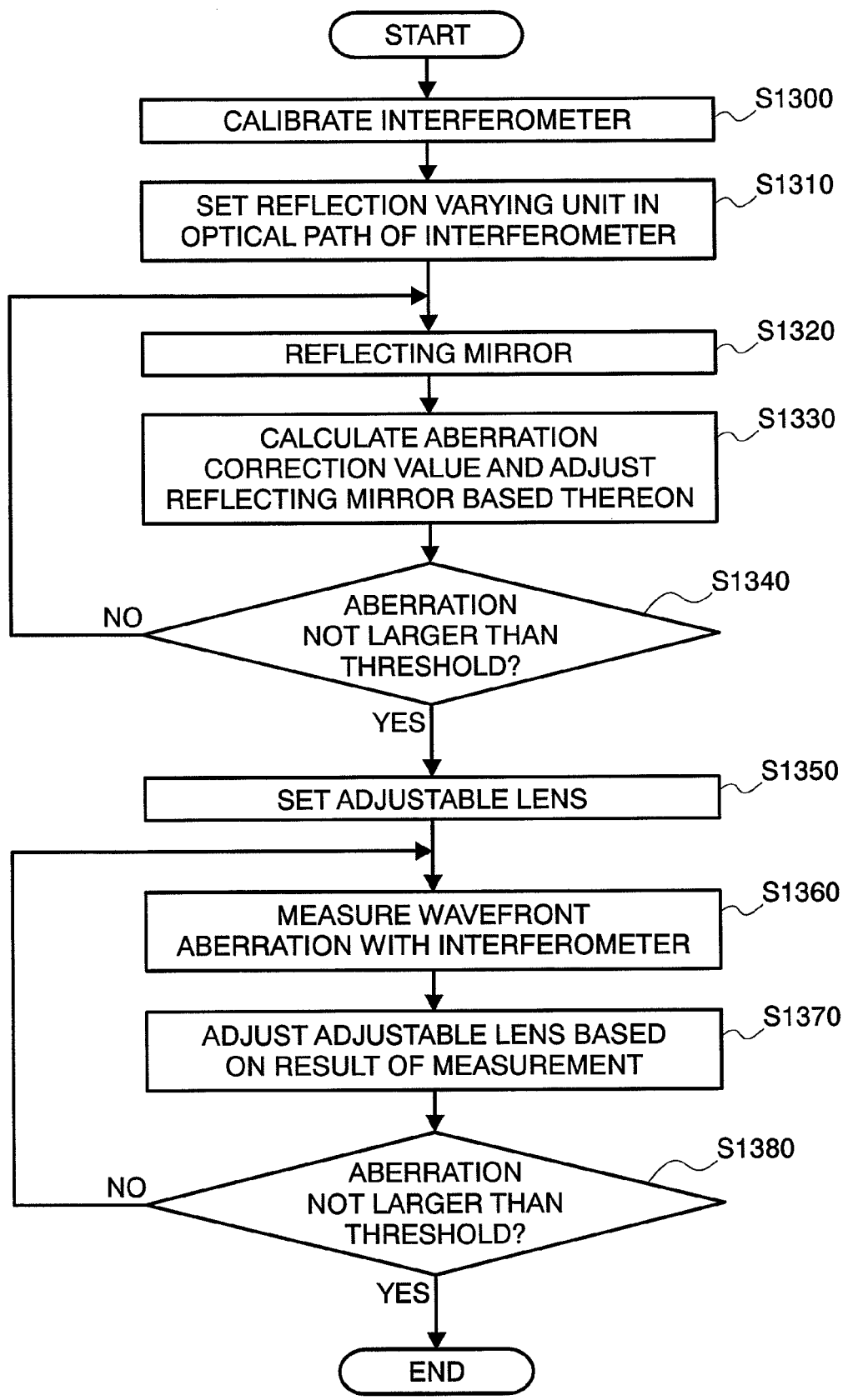
FIG. 11 is a flowchart illustrating a procedure of the adjustment of the front lens group illustrated in FIG. 10.
Figure 12:
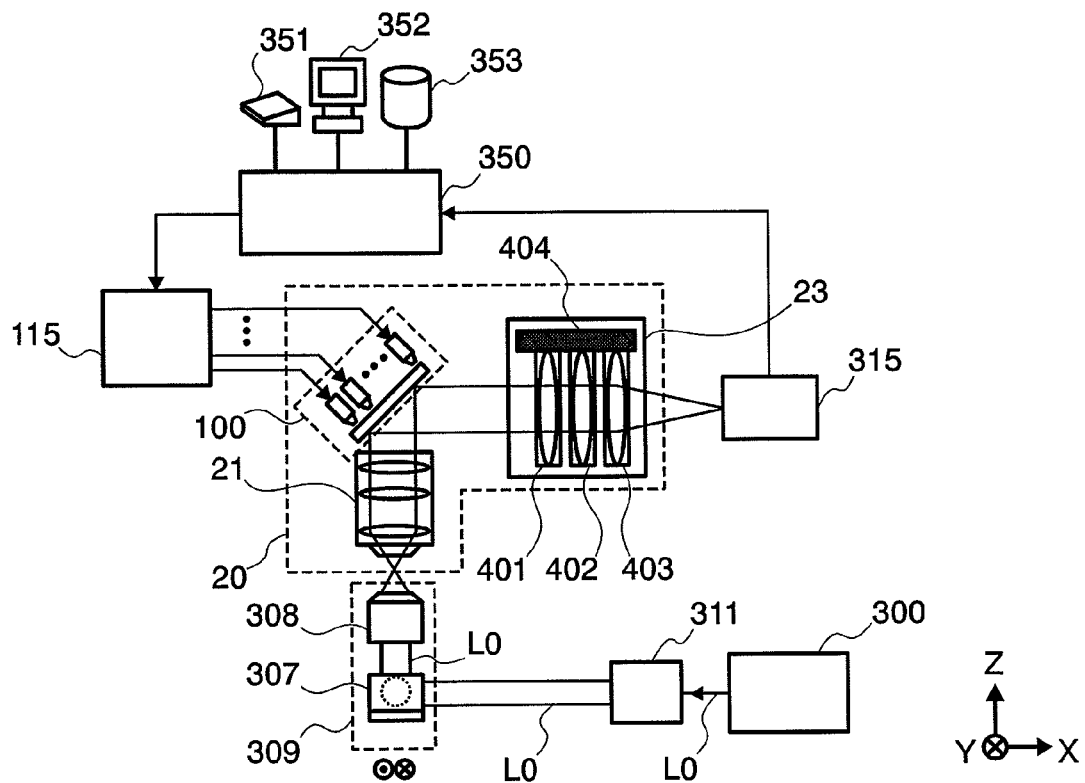
FIG. 12 is a diagram illustrating an overall adjustment of the detection optical system.

There will be described an example of a procedure of adjusting a front lens group system 18 of the detection optical system 20 which includes the objective lens 21 and the reflection varying unit 100, with the interferometer apparatus 360, by referring to a flowchart of FIG. 11.

Figure 8A:
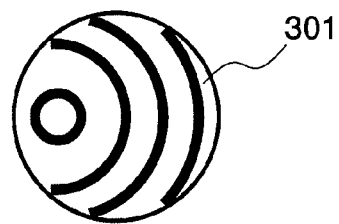
FIG. 8A is a view of interference fringes as observed with the interferometer apparatus and occurring when the rear lens group is not properly adjusted.
Figure 8B:
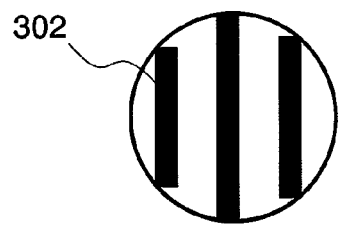
FIG. 8B is a view of interference fringes observed with the interferometer apparatus and occurring when the rear lens group is properly adjusted.

Initially, in the interferometer apparatus 360 shown in FIG. 6, the reflection varying unit 100 is switched or replaced with the mirror 340 so that the mirror 340 is set in the optical path, and the reference mirror 330 is roughly adjusted so that the interference fringes 301 shown in FIG. 8A appear on a screen of the display device 352, and then more finely adjusted to make the interference fringes 301 appear like interference fringes 302 as shown in FIG. 8B. In this way, the interferometer apparatus 360 is calibrated (S1300).

Then, the reflection varying unit 100 is switched or replaced with the mirror 340 (S1310). A flatness of the reflecting mirror 105 of the reflection varying unit 100 is measured with the fringe analyzing apparatus 350, and the amount of the wavefront aberration is calculated (S1320). Based on the obtained amount of the wavefront aberration, a correction value is calculated, and the reflecting mirror 105 of the reflection varying unit 100 is deformed by driving the actuators 110 so as to adjust the amount of the aberration (S1330).

After the adjustment, the interference fringes are again observed on the monitor of the display device 352 and the aberration amount is calculated with the fringe analyzing apparatus 350. It is determined whether the aberration amount is not larger than the predetermined threshold (S1340). When the aberration amount is larger than the predetermined threshold, steps S1320-1340 are repeated.

Figure 10:
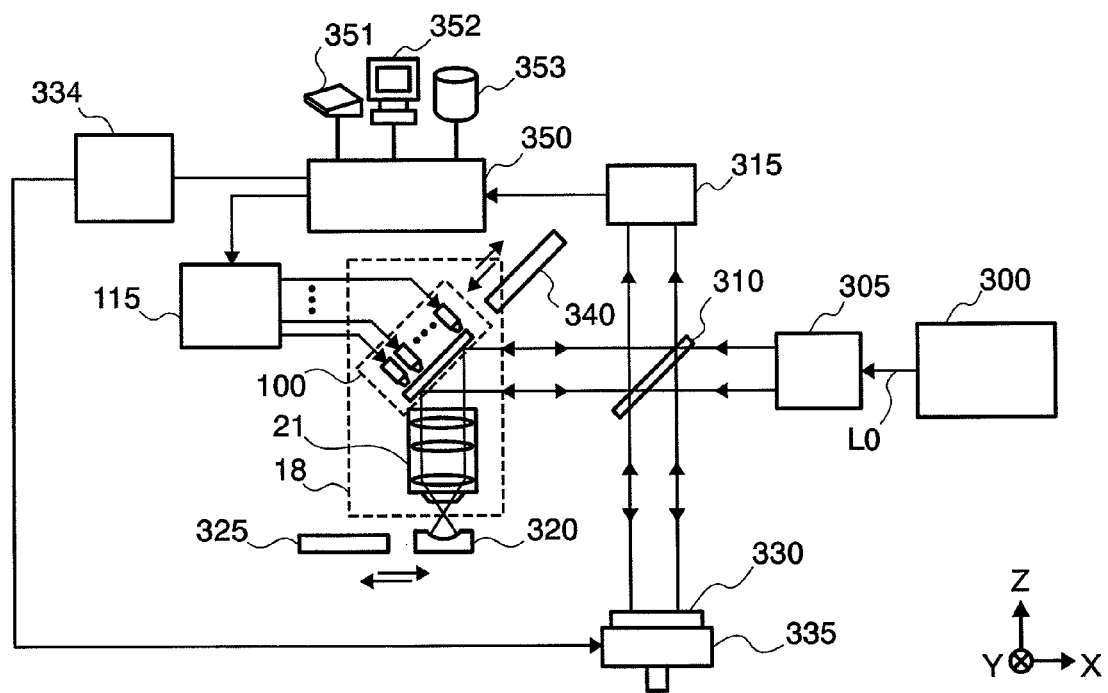
FIG. 10 is a diagram illustrating how a front lens group of the detection optical system is adjusted using the interferometer apparatus.

Next, as shown in FIG. 10, the front lens group system 18 is set in the detection optical system (S1350), and the wavefront aberration is measured with the fringe analyzing apparatus 350 (S1360). The front lens group system 18 as an adjustable lens is adjusted based on the measurement of the aberration, so that the shape of the interference fringes on the monitor screen of the display device 352 is changed from that of FIG. 8A to that of FIG. 8B (S1370). The measurement of the aberration with the fringe analyzing apparatus 350 is again made, and it is determined whether the aberration amount is not larger than the predetermined threshold (S1380). When the aberration amount is larger than the threshold, the steps S1360-S1380 are repeated.

The front lens group system 18 as has been adjusted according to the above-described steps, is combined with the rear lens group system 19, and then an overall adjustment of the detection optical system 20 is implemented. Hereinafter, there will be described how to adjust the detection optical system 20 as a whole, by referring to FIG. 12.

The laser beam L0 emitted from the laser light source 300 is enlarged by a beam expander optical system 311, and bent by a mirror (not shown) to the Y-axis direction, and then reflected in the Z-axis direction by the mirror 307 to enter the condenser lens 308. Thereafter, the laser beam L0 forms a laser spot at a position of a front focus of the objective lens 21, namely, at a surface to be inspected. The laser spot enters the objective lens 21 and forms a spot image at the image forming position of the detection optical system 20, and thus enters the detecting device 315 disposed at the image forming position. The detecting device 315 outputs an image signal to the fringe analyzing apparatus 350.

The fringe analyzing apparatus 350 measures an aberration of the spot image based on the image signal from the detecting device 315, and a relative position between the front lens group system 18 and the rear lens group system 19 is adjusted so as to minimize the aberration. The measurement of the aberration and the positional adjustment of the lens system are repeated until the aberration amount lowers below the predetermined threshold. A result of the adjustment is stored in a storage device 353, as data associated with that detection optical system 20, and used as reference data after installation of the detection optical system 20 in the defect inspecting apparatus.

Figure 14:
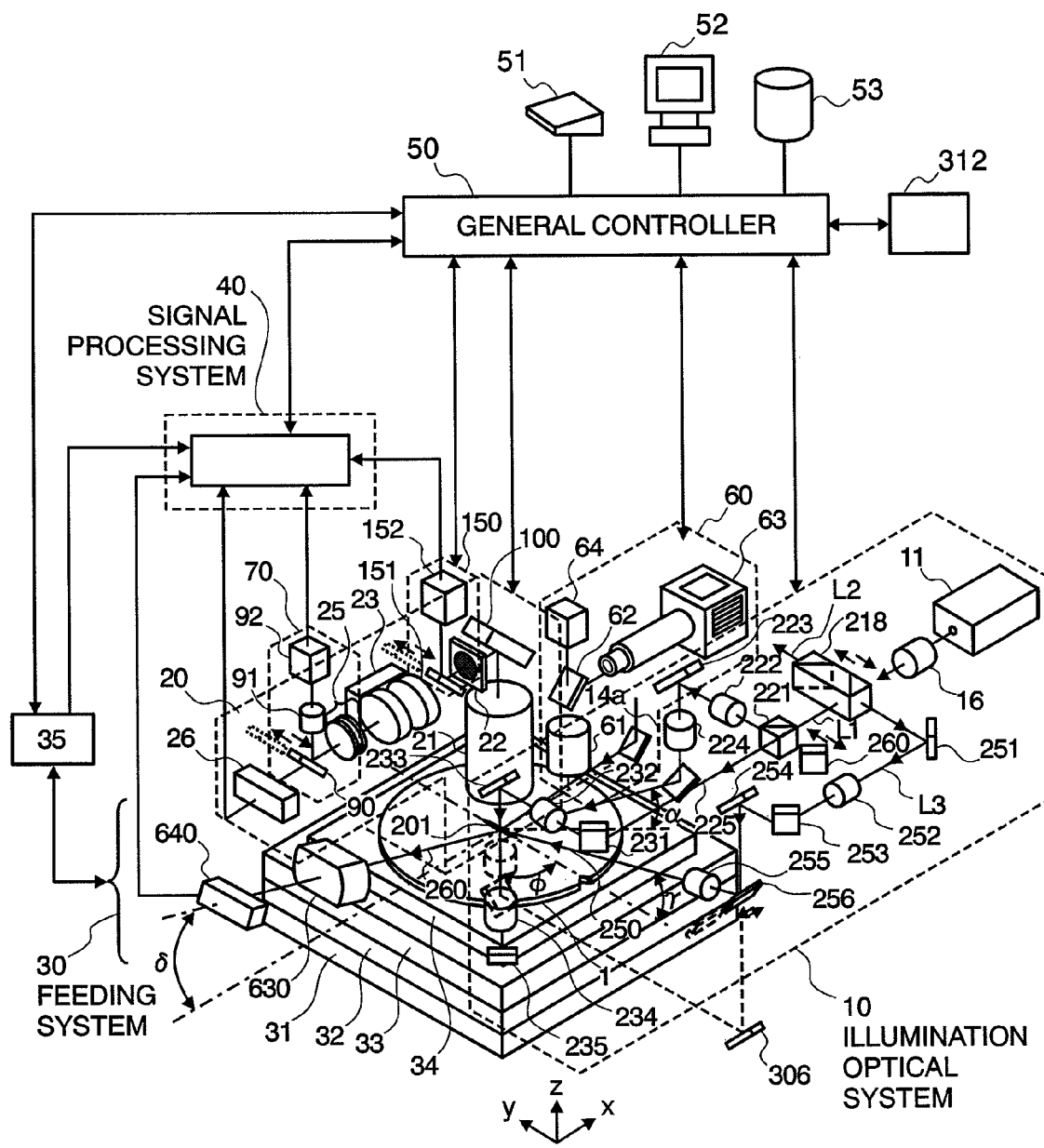
FIG. 14 shows a general structure of the defect inspecting apparatus.

The thus adjusted detection optical system 20 is installed in the defect inspecting apparatus as shown in FIG. 14, and the image formation performance of the detection optical system 20 can be maintained at the level at the time of the production, by the wavefront measuring optical system 150.

The number of lenses of the objective lens 21 and that of the image forming lens 23 as components of the detection optical system 20 are expected to increase. An aspherical lens may be used to reduce the number of the lenses significantly. This can be effective to reduce the weight of the detection optical system 20, and the number of assembly steps thereof.

A foreign particle/defect inspection is required for a multilayer wafer, too, on a surface of which a transparent film (e.g., an oxide film) is formed. That is, a multilayer wafer is produced by repeating a step of forming a pattern on a transparent film. In an inspection of foreign particle on a wafer with an oxide film thereon, there are increasing needs for detecting only foreign particles on a surface of the oxide film. Basically, it is possible to inhibit reflecting light from a substrate, e.g., light diffracted by a pattern, from affecting the inspection, by having the illumination angle α small. However, by making the illumination angle α small, a part of the scattered light from a foreign particle on the side of the regular reflection with respect to the illumination beam, i.e., forward scattering light, increases, while entrance of the scattered light into the detection optical system disposed above decreases, thereby making a stable detection of foreign particle impossible.

Hence, the invention uses the apparatus shown in FIG. 14 to detect foreign particles. Although the illumination optical system 10 has the same structure as shown in FIG. 2B, the optical elements disposed along the optical path L2 starting from the splitting optical element 218, and reference numerals of some parts corresponding to those in FIG. 2B, are omitted in FIG. 14. In the system shown in FIG. 14, a laser beam emitted from the light source 11 is enlarged in its diameter by the beam expander optical system 16, and reflected by the splitting optical element 218 in the direction of the optical path L3, to irradiate the wafer 1 with the slit-like beam 201 from an illumination angle γ from the illumination direction 250, via the mirror 251, the beam diameter correction optical system 252, the mirrors 253, 254, 256, and the cylindrical lens 255. A detection optical system including an image forming lens 630 and a detecting device 640 is disposed in a direction 260 that intersects the illumination direction 250 and forms a detection angle δ (i.e., an inclination angle with respect to the surface of the wafer 1), thereby enabling to detect side scarred light from the foreign particle on the surface of the thin film on the wafer, by irradiating the wafer 1 with the slit-like beam 201 from the illumination direction 250. A light receiving surface of the detecting device 640 and a surface area irradiated with the slit-like beam 201 are in a positional relationship to enable formation of an image, and the image formation magnification of the image forming lens 630 is set such that the light receiving surface of the detecting device can encompass an entire illuminating range of the slit-like beam 201.

By having the detection system in the positional relationship to form an image, an influence of stray light from an object other than the object to be inspected is prevented, while the speed of the inspection is increased since parallel processing is possible. During the inspection, the light receiving surface of the detecting device is controlled by an autofocus control system (not shown) so as to encompass the entire illuminating range of the slit-like beam 201 in order that the surface of the wafer is at a predetermined position in the Z-axis direction. As the detecting device 640, a TDI image sensor is employed, for instance, similarly to the detecting device 26. It is possible to dispose a spatial filter having the same function as the spatial filter 22 described with respect to FIG. 1, in the optical path, in order to block reflected diffracted light from the pattern. The illumination may be made from the direction 220 or 230 shown in FIGS. 2B and 2C. However, it is desirable that the illuminating means and the detection optical system including the image forming lens 630 and the detecting device 640 are disposed so as not to interfere, and the illumination and detection systems are disposed in directions and at angles that can prevent an influence of the reflected light from the substrate such as diffracted light from the pattern, namely, at optimum positions empirically obtained.

Figure 15:
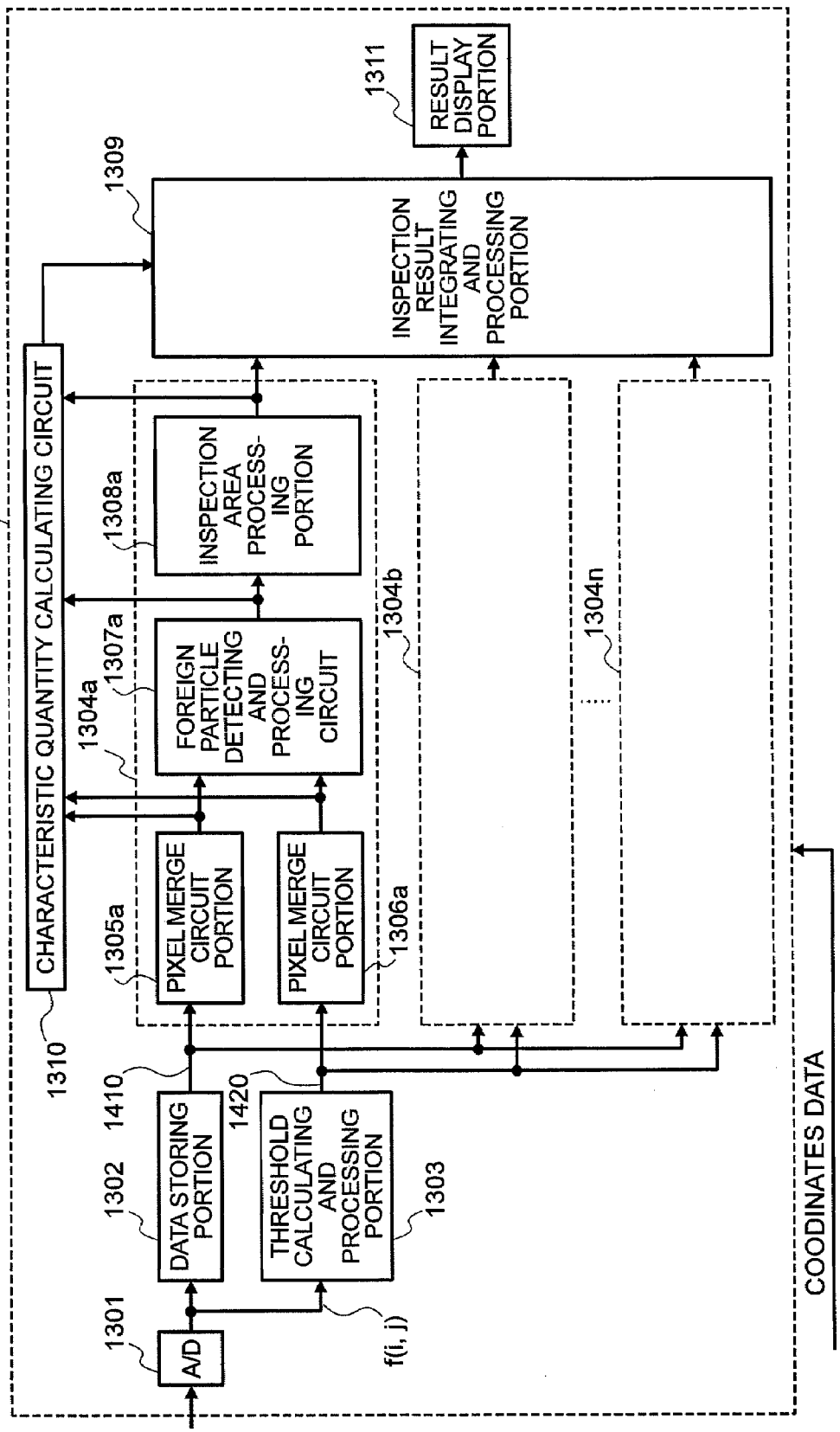
FIG. 15 is a block diagram of a signal processing system shown in FIG. 1.

There will be described the signal processing system 40 which processes signals outputted from the light detecting device 26 that receives the reflected diffracted light from the wafer 1 and implements photoelectric conversion, by referring to FIG. 15. The system shown in FIG. 15 is an example where a single signal processing circuit is provided in the signal processing system 40. However, where the detecting device 26 has a plurality of output channels, it is necessary to provide, in the signal processing system 40, a plurality of circuits each having the same structure as the signal processing system of the present embodiment.

The signal processing system 40 includes: an A/D converter 1301; a data storing portion 1302 that stores a detected image signal f (i, j) as A/D-converted; a threshold calculating and processing portion 1303 that implements a threshold calculation based on the detected image signal; foreign particle detecting and processing portions 1304a-1304n each of which includes a plurality of circuits for implementing foreign particle detection processing for respective merge units, based on the detected image signal 1410 obtained from the data storing portion 1302, and a threshold image signal 1420 (Th(H), Th(Hm), Th(Lm), Th(L)) obtained from the threshold calculating and processing portion 1303; a characteristic quantity calculating circuit 1310 which calculates characteristic quantities such as an amount of scattered light from defect obtained by a detection with a low angle illumination, an amount of scattered light from defect obtained by a detection with a high angle illumination, and the number of detection pixels indicating a range of the defect; an inspection result integrating and processing portion 1309 that categorizes the defects such as minute/large foreign particles, pattern defect, and microscratch on the semiconductor wafer, based on the characteristic quantities of the respective merge units obtained from the characteristic quantity calculating circuit 1310; and a result display portion 1311.

Each of the foreign particle detecting and processing portions 1304a-1304n includes a pixel merge circuit 1305a-1305n, 1306a-1306n, a foreign particle detecting and processing circuit 1307a-1307n, and an inspection area processing portion 1308a-1308n, correspondingly to merge operators of 1×1, 3×3, 5×5 . . . and n×n, respectively.

The signal obtained by the light detecting device 26 is digitized by the A/D converter 1301, and the detected image signal f(i, j) 1410 is stored in the data storing portion 1302, as well as sent to the threshold calculating and processing portion 1303. The threshold calculating and processing portion 1303 calculates the threshold image signal Th(i, j) 1420 for foreign particle detection, and the foreign particle detecting and processing circuit 1307 of each merge operator detects foreign material, based on the signal processed by the pixel merge circuits 1305, 1306.

The inspection area processing portion 1308 processes the signal of detected foreign material and the threshold image signal depending on the place of the detection. At the same time, based on the signals obtained from the pixel merge circuits 1305a-1305n, 1306a-1306n, the foreign particle detecting and processing circuits 1307a-1307n, the inspection area processing portions 1308a-1308n, that are included in the foreign particle detecting and processing portions 1304a-304n of the respective merge operators, the characteristic quantity calculating circuit 1310 calculates the characteristic quantities (e.g., an amount of the scattered light obtained with high angle illumination, an amount of scattered light obtained with low angle illumination, the number of detection pixels with defect), and the inspection result integrating and processing portion 1309 integrates the foreign particle signal with the characteristic quantities, and a result of the inspection is presented on a result display portion 1311.

More specifically, initially, the A/D converter 1301 is a circuit having a function to convert an analog signal obtained by the light detecting device 26 into a digital signal, and the number of bits of the conversion is desirably 8 bits to 12 bits, since when the bit number is too small, the resolution of the signal processing lowers, making detection of minute light difficult, while when the bit number is too large, the A/D converter is expensive, increasing the cost of the apparatus. The data storing portion 1302 is a circuit for storing the digital signal.

Figure 16:
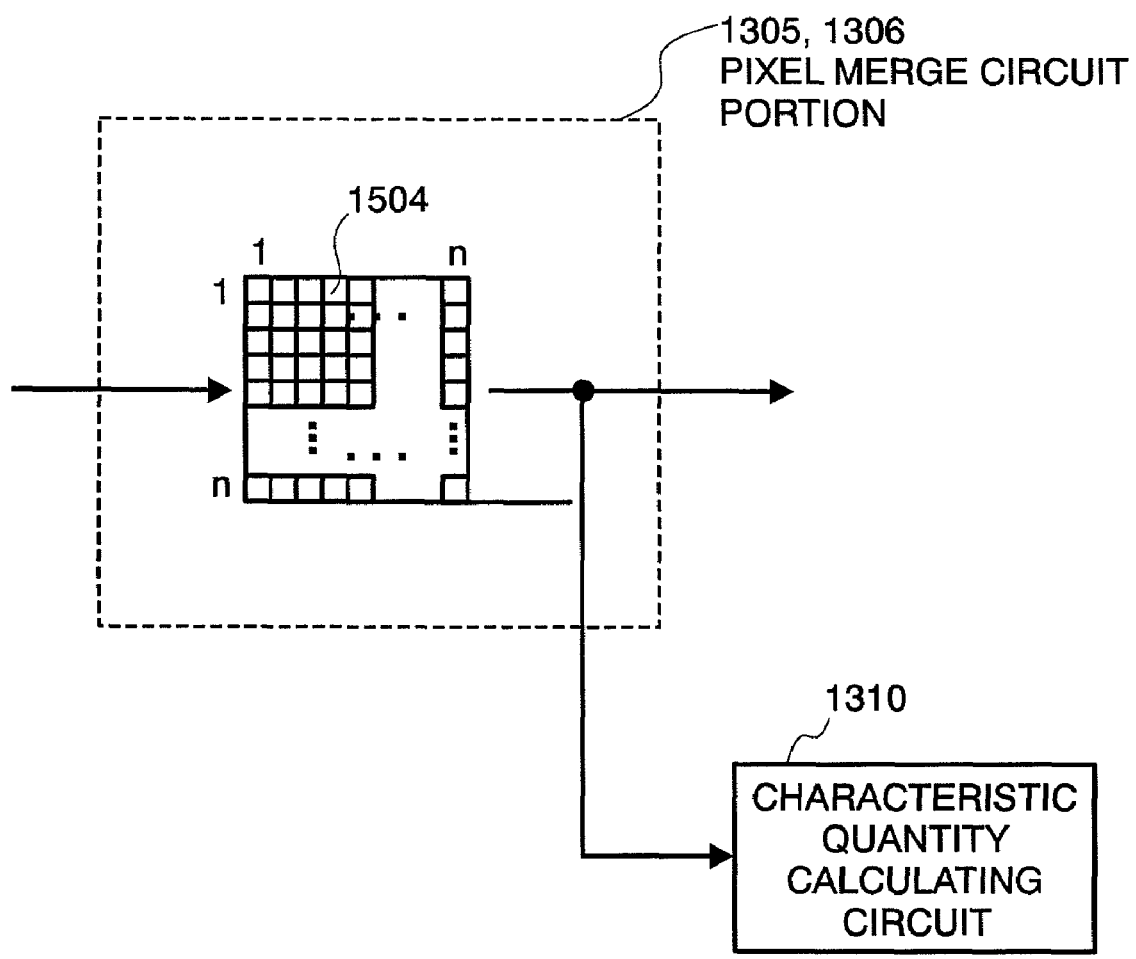
FIG. 16 is a diagram illustrating a threshold calculating and processing portion.

Then, by referring to FIG. 16, the pixel merge circuits 1305, 1306 will be described. The pixel merge circuits 1305a-1305n, and 1306a-1306n, are constituted by different merge operators 1504.

The merge operators 1504 function to integrate, in a range of n×n pixels, the detected image signal f(i, j) 1410 obtained from the data storing portion 1302, and the difference threshold image signal 1420 constituted by a detection threshold image signal Th(H), a detection threshold image signal Th(L), a verification threshold image signal Th(Hm), and a verification threshold image signal Th(Lm), and obtained from the threshold calculating and processing portion 1303. For instance, the merge operator is a circuit that outputs a mean value of n×n pixels.

For example, the pixel merge circuits 1305a, 1306a is constituted by a merge operation for merging of 1×1 pixel, the pixel merge circuits 1305b, 1306b is constituted by a merge operator for merging 3×3 pixels, the pixel merge circuits 1305c, 1306c is constituted by a merge operator for merging 5×5 pixels, . . . and the pixel merge circuits 1305n, 1306n is constituted by a merge operator for merging n×n pixels. The merge operator for merging of 1×1 pixel outputs the input signals 1410, 1420 without any processing.

As described above, the threshold image signal is constituted by four image signals (Th(H), Th(Hm), Th(Lm), Th(L)), each of the pixel merge circuit portions 1306a-1306n requires four merge operators Op. Hence, each of the pixel merge circuits 1305a-1305n outputs merged detected image signals 431a-431n that are the detected image signal as processed or merged by the merge operators 1504. Meanwhile, the pixel merge circuit portions 1306a-1306n outputs merged threshold image signals 441a (441a1-441a4)-441n (441n1-441n4) that are the four threshold image signals (Th(H), Th(Hm), Th(Lm), Th(L)) as merged by merge operators Op1-Opn. The merge operators in the pixel merge circuit portions 1306a-1306n are the same.

The effect of merging of the pixels will be illustrated. In a foreign particle inspection, not only a minute foreign particle but also a large thin-film shaped foreign particle that spreads in a range of several micrometers should be detected without oversight. However, the detected image signal from such a thin-film shaped foreign particle is not necessarily strong, the S/N ratio of the pixel-by-pixel detected image signal is low, which may cause an oversight. Thus, the unit of the detection is n×n pixels corresponding to the size of the thin-film shaped foreign particle and a convolution calculation is implemented, in order to improve the S/N ratio.

There will be now described the inspection area processing portions 1308a-1308n. The inspection area processing portions 1308a-1308n operate to process the foreign particle/defect detection signals obtained from the foreign particle detecting and processing circuits 1307a-1307n with an identification of the chip in question, namely, to delete data of an area (including one inside a chip) not requiring the inspection, to vary the detection sensitivity for each area (including one inside a chip), and to select an area desired to inspect.

The inspection area processing portions 1308a-1308n may operate such that when an area on the object substrate 1 does not require a high detection sensitivity, a threshold obtained by a threshold calculating portion 1411 of the threshold calculating and processing portion 1303 is set at a high level at that area, or such that data on a foreign particle only in an area desired to be inspected is maintained based on coordinates of the foreign particle and from data of the foreign particle outputted from the foreign particle detecting and processing circuits 1307a-1307n.

The area where the detection sensitivity is not required to be high is, for instance, an area where the density of the circuit pattern on the object substrate 1 is low. Reducing the detection sensitivity efficiently reduces the number of detected foreign particles/defects. That is, a defect inspecting apparatus with high sensitivity may detect several tens of thousands of foreign particles, in some situations. However, the thing really matters is foreign particles in an area where the circuit pattern is present, and it is a shortcut to take measures against the significant foreign particles in improving the yield rate in the device production.

However, when the entire area on the object substrate 1 is inspected with a same degree of sensitivity, the significant and non-significant foreign particles are mixed, thereby making it difficult to extract the significant foreign particles. Hence, the inspection area processing portions 1308a-1308n lower the detection sensitivity for the area where the circuit pattern is not present and thus which does not much affect the yield rate, based on CAD information or threshold map information in the chip, so as to efficiently extract the significant foreign particles. However, the way of extracting the significant foreign particles is not limited to the method of varying the detection sensitivity, but may be otherwise. For instance, the significant foreign particles may be extracted by categorizing the foreign particles, as described later, or based on the size of the foreign particles.

There will be described the inspection result integrating and processing portion 1309 and its inspection the result display portion 1311. The inspection result integrating and processing portion 1309 integrates the results of the foreign particles that are processed in parallel by the pixel merge circuits 1305, 1306, integrates the characteristic quantities calculated by the characteristic quantity calculating circuit 1310 and the results of the foreign particle detection, and send the integrated result to the result display portion 1311. This inspection result integration processing is desirably implemented by a PC or others so as to facilitate a change in the content of the processing.

First, there will be described the characteristic quantity calculating circuit 1310. The characteristic quantities represent the characteristics of the detected foreign particle and the defect, and the characteristic quantity calculating circuit 1310 is a processing circuit which calculates the characteristic quantities, that may be, for instance, an amount of the reflected diffracted light (i.e., an amount of the scattered light) (Dh, Dl) from a foreign material or a defect with high angle and low angle illumination, the number of detection pixels, the shape of the area where the detection of foreign particle is implemented, and the direction of a principal axis of inertia, the detected place on the wafer, the kind of the circuit pattern of the substrate, a threshold value used when detecting foreign particle.

[Employment of a microscope] The defect inspecting apparatus of the embodiment includes the observation optical system 60 with which the foreign particle detected by the inspection is confirmable, as shown in FIG. 17. By moving the stages 31, 32, the detected foreign particle on the wafer 1 (including false information) is moved into a field of view of a microscope of the observation optical system 60, and an image of the microscope is observed.

An advantage of including the observation optical system 60 is that the detected foreign particles is immediately observable, without moving the wafer to a review device such as SEM. By instantaneously observing the foreign particle detected by the defect inspecting apparatus, a causal of the foreign particle is quickly identified. An image of the foreign particle taken by the TV camera 64 of the observation optical system 60 is displayed on a color monitor commonly used for a personal computer, and thus an inspection around the coordinates of the detected foreign particle by a local irradiation with a laser beam and stage scanning is possible, and also there is a function to display an image of scattered light from the foreign particle and a marked position of the foreign particle, on the monitor. Thus, it is possible to confirm whether a foreign particle is actually detected or not. The local image taken by stage scanning enables comparison or confirmation at the moment since an image of a die next to the die in which a foreign particle is detected can be taken.

A light source of the observation optical system 60 may be visible light (e.g., white light). Alternatively, the observation optical system 60 may be a microscope whose light source is ultraviolet light. To observe a particularly minute foreign particle, a microscope with high resolution, e.g., a microscope using ultraviolet light is desirable. When a microscope using visible light is employed, color information on the foreign particle is obtained, thereby facilitating recognition of the foreign particle.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

The invention claimed is:

1. A method for inspecting a specimen using an optical inspection apparatus, including the steps of:
   obliquely illuminating a specimen with light shaped long in one direction emitted from an illuminating optical unit of the optical inspection apparatus;
   forming, with an optical detection unit of the optical inspection apparatus, an optical image on an image sensor of the optical detection unit with light scattered from the specimen;
   detecting the optical image formed on the image sensor with the image sensor; and
   processing a signal output from the image sensor by the detection of the optical image with an image processor of the optical inspection apparatus,
   wherein, in the step of forming the optical image, said optical detection unit is adjusted so that an image formation performance of the optical detection unit is within a predetermined range.

2. A method according to claim 1, wherein said image formation performance of the optical detection unit is related to a wavefront aberration of the optical detection unit.

3. A method according to claim 1, wherein a state in which said image formation performance is adjusted is a state in which a wavefront aberration of the optical detection unit is adjusted within a predetermined range.

4. A method according to claim 3, wherein said wavefront aberration of the optical detection unit is calculated from a signal obtained by detecting light passed through a table on which the specimen is mounted.

5. A method for inspecting a specimen using an optical inspection apparatus, including the steps of:
   obliquely illuminating a specimen with light shaped long in one direction emitted from an illuminating optical unit of the optical inspection apparatus;
   forming, with an optical detection unit of the optical inspection apparatus, an optical image on an image sensor of the optical detection unit with light scattered from the specimen;
   detecting the optical image formed on the image sensor with the image sensor; and
   processing a signal output from the image sensor by the detection of the optical image with an image processor of the optical inspection apparatus,
   wherein, in the step of forming the optical image, said optical detection unit is adjusted so that a difference of an image formation performance of the optical detection unit between another optical inspection apparatus is less than a predetermined value.

6. A method according to claim 5, wherein said image formation performance of the optical detection unit is related to a wavefront aberration of the optical detection unit.

7. A method according to claim 5, wherein a state in which said difference of an image formation performance of the optical detection unit between the optical inspection apparatus and another optical inspection apparatus is adjusted to be less than a predetermined value of image formation performance is a state in which a wavefront aberration of the optical detection unit between the optical inspection apparatus and another optical inspection apparatus is adjusted to be less than a predetermined value.

8. A method according to claim 7, wherein said wavefront aberration of the optical detection unit is calculated from a signal obtained by detecting light passed through a table on which the specimen is mounted.

9. An optical inspection apparatus, comprising:
a table on which a specimen to be inspected is mounted, said table being movable in a plane;
an illuminating optical unit which obliquely illuminates a specimen mounted on the table with light shaped long in one direction;
an optical detection unit which forms an optical image with light scattered from the specimen illuminated by the light and detects the image with an image sensor; and
a processing unit which processes a signal output from the image sensor by the detection of the optical image with an image processor of the optical inspection apparatus,
wherein, said optical detecting unit forms the optical image on the image sensor of the optical detection unit which is adjusted in a state that an image formation performance of the optical detection unit is within a predetermined range.

10. An optical inspection apparatus according to claim 9, wherein said image formation performance of the optical detection unit is related to a wavefront aberration of the optical detection unit.

11. An optical inspection apparatus according to claim 9, wherein a state in which said image formation performance is adjusted is a state in which a wavefront aberration of the optical detection unit is adjusted to be within a predetermined range.

12. An optical inspection apparatus according to claim 11, wherein said wavefront aberration of the optical detection unit is calculated from a signal obtained by detecting light passed through the table.

13. An optical inspection apparatus, comprising:
a table which mounts a specimen to be inspected is mounted, said table being movable in a plane;
an illuminating optical unit which obliquely illuminates a specimen mounted on the table with light shaped long in one direction;
an optical detection unit which forms an optical image with light scattered from the specimen illuminated by the light and detects the image with an image sensor; and
a processing unit which processes a signal output from the image sensor by the detection of the optical image with an image processor of the optical inspection apparatus,
wherein said optical detection unit is so adjusted that a difference in an image formation performance between the optical detection unit of the optical inspection apparatus and an optical detection unit of another optical inspection apparatus to be less than a predetermined value.

14. An optical inspection apparatus according to claim 13, wherein said image formation performance of the optical detection unit is related to a wavefront aberration of the optical detection unit.

15. An optical inspection apparatus according to claim 13, wherein a state in which said optical detection unit is adjusted is a state in which a difference between a wavefront aberration of the optical detection unit of the optical inspection apparatus and a wavefront aberration of an optical detection unit of another optical inspection apparatus are adjusted to be less than a predetermined value.

16. An optical inspection apparatus according to claim 15, wherein said wavefront aberration of the optical detection unit is calculated from a signal obtained by detecting light passed through the table with the optical detection unit.

* * * * *